US012703687B2

(12) United States Patent
Liang et al.

(10) Patent No.: US 12,703,687 B2
(45) Date of Patent: Aug. 11, 2026

(54) TETRAHYDROISOQUINOLINE COMPOUND AS POTASSIUM CHANNEL MODULATOR AND PREPARATION AND APPLICATION THEREOF

(71) Applicant: Shanghai Zhimeng Biopharma, Inc., Shanghai (CN)

(72) Inventors: Bo Liang, Shanghai (CN); Gang Liu, Shanghai (CN); Huanming Chen, Shanghai (CN)

(73) Assignee: SHANGHAI ZHIMENG BIOPHARMA, INC., Shanghai (CN)

( * ) Notice: Subject to any disclaimer, the term of this patent is extended or adjusted under 35 U.S.C. 154(b) by 1069 days.

(21) Appl. No.: 17/791,613

(22) PCT Filed: Aug. 5, 2021

(86) PCT No.: PCT/CN2021/110991

§ 371 (c)(1),
(2) Date: Jul. 8, 2022

(87) PCT Pub. No.: WO2022/028548

PCT Pub. Date: Feb. 10, 2022

(65) Prior Publication Data

US 2023/0077155 A1 Mar. 9, 2023

(30) Foreign Application Priority Data

Aug. 7, 2020 (CN) ......................... 202010790306.7

(51) Int. Cl.

| | |
|---|---|
| ***C07D 217/04*** | (2006.01) |
| ***C07D 223/16*** | (2006.01) |
| ***C07D 401/04*** | (2006.01) |
| ***C07D 409/04*** | (2006.01) |
| ***C07D 471/04*** | (2006.01) |

(52) U.S. Cl.

CPC ......... *C07D 217/04* (2013.01); *C07D 223/16* (2013.01); *C07D 401/04* (2013.01); *C07D 409/04* (2013.01); *C07D 471/04* (2013.01); *C07B 2200/05* (2013.01)

(58) Field of Classification Search

CPC .................................................... C07D 217/04

See application file for complete search history.

(56) References Cited

FOREIGN PATENT DOCUMENTS

| | | |
|---|---|---|
| CN | 103508960 A | 1/2014 |
| CN | 107108556 A | 8/2017 |
| CN | 107814785 A | 3/2018 |
| CN | 110511220 A | 11/2019 |
| RU | 2468010 C2 | 11/2012 |

OTHER PUBLICATIONS

Jenkinson, Donald H. "Potassium channels—multiplicity and challenges" British Journal of Pharmacology (2006) 147, S63-S71.*

Brown, D. A. "Some Pharmacological Properties of Neural KCNQ Channels." Neurophysiology 2002, 34(2-3), 91-94.*

Fritch, Paul C.; "Novel KCNQ2/Q3 Agonists as Potential Therapeutics for Epilepsy and Neuropathic Pain." Journal of Medicinal Chemistry, 2010 53(2), 887-896.*

Amato, George "N-Pyridyl and Pyrimidine Benzamides as KCNQ2/Q3 Potassium Channel Openers for the Treatment of Epilepsy." ACS Medicinal Chemistry Letters, 2011 2(6), 481-484.*

Du "M-type K+ channels in peripheral nociceptive pathways" British Journal of Pharmacology (2018) 175 2158-2172.*

Korsgaard, M. P. "Anxiolytic effects of Maxipost (BMS-204352) and retigabine via activation of neuronal Kv7 channels." J. Pharmacol. Exp. Ther. 314, 282-292.*

G. Blackburn-Munro, "Retigabine: Chemical Synthesis to Clinical Application" CNS Drug Reviews 2005, vol. 11, No. 1, pp. 1-20.*

Friedman "KCNQ channel openers reverse depressive symptoms via an active resilience mechanism" Nature Communications 2016, | 7:11671, 1-7.*

Fontan-Lozano "The M-current inhibitor XE991 decreases the stimulation threshold for long-term synaptic plasticity in healthy mice and in models of cognitive disease" Hippocampus 2011, 21(1), 22-32 (abstract only).*

Song "The facilitating effect of systemic administration of Kv7/M channel blocker XE991 on LTP induction in the hippocampal CA1 area independent of muscarinic activation" Neuroscience Letters 461 (2009) 25-29.*

Xia "Voltage-gated potassium channels control extended access cocaine seeking: a role for nucleus accumbens astrocytes" Neuropsychopharmacology (2024) 49:551-56.*

Shah "The role of fluorine in medicinal chemistry" Journal of Enzyme Inhibition and Medicinal Chemistry, Oct. 2007; 22(5): 527-540.*

Dyck et al. Journal of Neurochemistry 1986, 46, 399-404.*

Earl "2-Fluoro-4-pyridinylmethyl Analogues of Linopirdine as Orally Active Acetylcholine Release-Enhancing Agents with Good Efficacy and Duration of Action" Journal of Medicinal Chemistry, 1998, vol. 41, No. 23 4615-4622.*

Int'l Search Report issued Oct. 19, 2021 in Int'l Application No. PCT/CN2021/110991.

Office Action with Search Report issued Jan. 31, 2023 in RU Application No. 2022119949.

* cited by examiner

*Primary Examiner* — David K O'Dell

(74) *Attorney, Agent, or Firm* — Panitch Schwarze Belisario & Nadel LLP

(57) ABSTRACT

A tetrahydroisoquinoline compound as a potassium channel modulator and preparation and application thereof. Specifically, the compound has the structure as shown in formula A.

Formula (A)

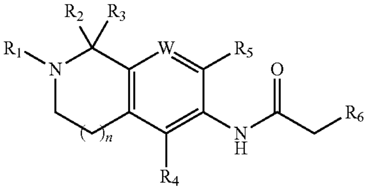

13 Claims, No Drawings

TETRAHYDROISOQUINOLINE COMPOUND AS POTASSIUM CHANNEL MODULATOR AND PREPARATION AND APPLICATION THEREOF

CROSS-REFERENCE TO RELATED APPLICATIONS

This application is a Section 371 of International Application No. PCT/CN2021/110991, filed Aug. 5, 2021, which was published in the Chinese language on Feb. 10, 2022, under International Publication No. WO 2022/028548 A1, which claims priority under 35 U.S.C. § 119(b) to Chinese Application No. 202010790306.7, filed Aug. 7, 2020, the disclosures of all of which are incorporated herein by reference.

TECHNICAL FIELD

The invention relates to the field of biomedicine, in particular to tetrahydroisoquinoline compound as potassium channel modulator and preparation and application thereof.

BACKGROUND ART

Kv7 potassium channel is a type of voltage-dependent potassium ion channel with low threshold activation, slow activation and non-inactivation. The Kv7 potassium channel has five family members (Kv7.1-Kv7.5), all of which have similar topology, namely functional channel composed of four subunits, and each subunit contains six transmembrane fragments (S1-S6). Among which, S4 is a voltage sensing region which plays an important role in sensing membrane potential changes and controlling conformational changes; SS-S6 is the main components of the channel aperture region, and is the main combination and action region of potassium channel openers. Kv7.1 potassium channel is a non-neuronal pathway, which is distributed in the outer peripheral tissue, expressed in the heart to mediate myocardial Iks, and its mutation can lead to Long Q-T syndrome. Kv7.2-Kv7.5 potassium channel is the basis of neuronal M current, is widely distributed in the nervous system, and has a variety of physiological activity. Kv7.2 and Kv7.3 potassium channel gene mutation can lead to a variety of different epilepsy patterns, such as Benign familial neonatal convulsions (BFNC), which fully demonstrates the role of M current in regulating neuronal excitability. Kv7.4 potassium channel is highly expressed in the outer hair cells of the cochlea and brainstem auditory nucleus, and its mutation may cause hereditary deafness. Kv7.5 potassium channels are highly expressed in skeletal muscle and brain, and its mutation may cause retinopathy. Many diseases such as epilepsy, anxiety, deafness, etc., their common feature is high membrane excitability, and Kv7 potassium channels are the molecular basis of M current, which can be opened by sensing changes in membrane potential, so that the inhibitory potassium current is up-regulated, thus controlling membrane excitability so as to make the Kv7 potassium channels are of great significance in pain and mental illness represented by high nerve excitability.

Retigabine is a drug for treating epilepsy. It has been approved for marketing in the UK, Germany, and Denmark. Studies have confirmed that the role of Retigabine is related to the voltage-gated potassium ion channel (KCNQs), wherein its main mechanism of action is to regulate M-type potassium currents by acting on KCNQ2/3 channels.

Retigabine (RTG) is the first Kv7 potassium channel opener for assisting the treatment of adult partial-onset epilepsy marketed in 2011. In addition to anti-epilepsy, RTG can also be used to treat anxiety, neuralgia, neurodegenerative diseases, etc. RTG can effectively reduce or prevent seizures in a variety of epilepsy models. RTG shows effective anti-epileptic effects on both tonic seizures caused by the maximal electroshock seizure (MES) model and clonic seizures induced by PTZ. In addition, RTG can also prevent seizures caused by N-methyl-D-aspartate (NMDA), penicillin, picrotoxin, Kainic acid (KA), etc. The ignition model is suitable for screening a variety of antiepileptic drugs, and the effect of RTG on this model is stronger than other models. Due to the extensive effects of RTG on all Kv7 potassium channel members and other channels, its poor selectivity makes it potentially undesirable. A large number of literatures have reported that RTG has a high incidence of adverse events related to the central nervous system, which can lead to dizziness, fatigue, aphasia, speech disorders, balance disorders and other adverse reactions including kidney stones, urinary retention and other kidney and urinary system diseases, cardiac related diseases such as sudden cardiac arrest, transient non-sustained ventricular tachycardia, and can also cause retinal discoloration, blue/purple pigmentation on skin, nails and the like.

SUMMARY OF THE INVENTION

The purpose of the present invention is to provide a compound represented by formula A, a preparation method thereof, and its use as a potassium channel regulator.

In the first aspect of the present invention, it provides a compound represented by formula A or a pharmaceutically acceptable salt thereof, formula A

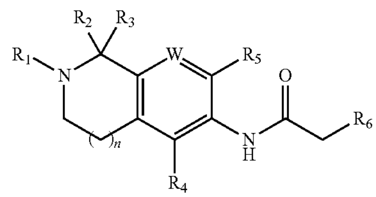

wherein, $R_1$ is selected from the substituted or unsubstituted group consisting of $C_{6-10}$ aryl and 4-7 membered heteroaryl containing 1-3 heteroatoms selected from N, O or S, and the substituted means being substituted by one or more substituents selected from the group consisting of halogen, nitro, cyano, $C_{1-6}$ alkyl, $C_{3-6}$ cycloalkyl, $C_{1-6}$ alkoxy, $C_{3-6}$ cycloalkoxy, halogenated $C_{1-6}$ alkyl, halogenated $C_{3-6}$ cycloalkyl, halogenated $C_{1-6}$ alkoxy, halogenated $C_{3-6}$ cycloalkoxy, $—NR_8R_9$ and ethynyl;

$R_2$ and $R_3$ are each independently selected from the group consisting of hydrogen, deuterium, halogen, $C_{1-6}$ alkyl and halogenated $C_{1-6}$ alkyl;

or $R_7$ and $R_3$ together with their respective connected C form $C_{3-10}$ cycloalkyl, and the cycloalkyl is optionally substituted by 1-3 substituents selected from the group consisting of hydrogen, halogen, $C_{1-6}$ alkyl and halogenated $C_{1-6}$ alkyl;

$R_4$ and $R_5$ are each independently selected from the group consisting of hydrogen, halogen, $C_{1-6}$ alkyl, $C_{1-6}$ alkoxy, halogenated $C_{1-6}$ alkyl and halogenated $C_{1-6}$ alkoxy;

$R_6$ is selected from the substituted or unsubstituted group consisting of $C_{1-6}$ alkyl, $C_{3-6}$ cycloalkyl, $C_{1-6}$ alkoxy and $C_{3-6}$ cycloalkoxy, and the substituted means being substituted by one or more substituents selected from the group consisting of halogen, nitro, cyano, $C_{1-6}$ alkyl, $C_{1-6}$ alkoxy, halogenated $C_{1-6}$ alkyl, halogenated $C_{1-6}$ alkoxy, $C_{2-6}$ alkenyl, $C_{2-6}$ alkynyl and $C_{3-6}$ cycloalkyl;

n is selected from the group consisting of 1, 2 and 3;

W is C—$R_7$ or N;

$R_7$ is selected from the group consisting of hydrogen, deuterium, halogen, cyano, $C_{1-6}$ alkyl, halogenated $C_{1-6}$ alkyl, $C_{1-6}$ alkoxy and halogenated $C_{1-6}$ alkoxy;

$R_8$ and $R_9$ are each independently selected from the group consisting of hydrogen, $C_{1-6}$ alkyl and halogenated $C_{1-6}$ alkyl;

or $R_8$ and $R_9$ together with their respective connected N form 3-10 membered azacycloalkyl.

In another preferred embodiment, $R_1$ is substituted or unsubstituted phenyl, and the substituted means being substituted by one or more substituents selected from the group consisting of halogen, cyano, $C_{1-6}$ alkyl, $C_{3-6}$ cycloalkyl, $C_{1-6}$ alkoxy, $C_{3-6}$ cycloalkoxy, halogenated $C_{1-6}$ alkyl, halogenated $C_{3-6}$ cycloalkyl, halogenated $C_{1-6}$ alkoxy, halogenated $C_{3-6}$ cycloalkoxy, —$NR_8R_9$ and ethynyl;

$R_2$ and $R_3$ are each independently selected from the group consisting of hydrogen and deuterium;

$R_4$ and $R_5$ are methyl;

$R_6$ is selected from the substituted or unsubstituted group consisting of $C_{1-6}$ alkyl and $C_{3-6}$ cycloalkyl, and the substituted means being substituted by one or more substituents selected from the group consisting of halogen, $C_{1-6}$ alkyl and $C_{3-6}$ cycloalkyl;

n is 1;

W is C—$R_7$;

$R_2$ is selected from the group consisting of hydrogen and halogen;

$R_8$ and $R_9$ are each independently $C_{1-6}$ alkyl.

In another preferred embodiment, $R_1$ is substituted or unsubstituted phenyl, and the substituted means being substituted by one or more substituents selected from the group consisting of halogen, cyano, $C_{1-6}$ alkyl, $C_{3-6}$ cycloalkyl, $C_{1-6}$ alkoxy, $C_{3-6}$ cycloalkoxy, halogenated $C_{1-6}$ alkyl, halogenated $C_{3-6}$ cycloalkyl, halogenated $C_{1-6}$ alkoxy, halogenated $C_{3-6}$ cycloalkoxy, —$NR_8R_9$ and ethynyl;

$R_2$ and $R_3$ are each independently selected from the group consisting of hydrogen and deuterium;

$R_4$ and $R_5$ are methyl;

$R_6$ is selected from the substituted or unsubstituted group consisting of $C_{1-6}$ alkyl and $C_{3-6}$ cycloalkyl, and the substituted means being substituted by one or more substituents selected from the group consisting of halogen and $C_{1-6}$ alkyl;

n is 1;

W is C—$R_7$;

$R_7$ is selected from the group consisting of hydrogen and halogen;

$R_8$ and $R_9$ are each independently $C_{1-6}$ alkyl.

In another preferred embodiment, $R_1$ is substituted or unsubstituted phenyl, and the substituted means being substituted by one or more substituents selected from the group consisting of halogen, cyano, $C_{1-6}$ alkyl, $C_{3-6}$ cycloalkyl, $C_{1-6}$ alkoxy, $C_{3-6}$ cycloalkoxy, halogenated $C_{1-6}$ alkyl, halogenated $C_{3-6}$ cycloalkyl, halogenated $C_{1-6}$ alkoxy, halogenated $C_{3-6}$ cycloalkoxy, —$NR_8R_9$ and ethynyl;

$R_2$ and $R_3$ are each independently selected from the group consisting of hydrogen and deuterium;

$R_4$ and $R_5$ are methyl;

$R_6$ is selected from the group consisting of

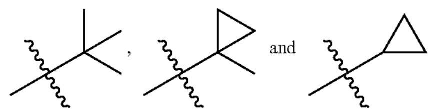

n is 1;

W is C—$R_7$;

$R_7$ is selected from the group consisting of hydrogen and halogen;

$R_8$ and $R_9$ are each independently $C_{1-6}$ alkyl.

In another preferred embodiment, $R_1$ is substituted or unsubstituted phenyl, and the substituted means being substituted by one or more substituents selected from the group consisting of halogen, cyano, $C_{1-6}$ alkyl, $C_{1-6}$ alkoxy, halogenated $C_{1-6}$ alkyl, —$NR_8R_9$ and ethynyl;

$R_2$ and $R_3$ are each independently selected from the group consisting of hydrogen and deuterium;

$R_4$ and $R_5$ are methyl;

$R_6$ is selected from the group consisting of

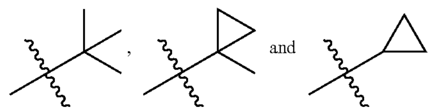

n is 1;

W is C—$R_7$;

$R_7$ is selected from the group consisting of hydrogen and halogen;

$R_8$ and $R_9$ are each independently $C_{1-6}$ alkyl.

In another preferred embodiment, $R_1$ is substituted or unsubstituted phenyl, and the substituted means being substituted by one or more substituents selected from the group consisting of halogen, cyano, $C_{1-6}$ alkyl, $C_{1-6}$ alkoxy, halogenated $C_{1-6}$ alkyl, —$NR_8R_9$ and ethynyl;

$R_2$ and $R_3$ are each independently selected from the group consisting of hydrogen and deuterium;

$R_4$ and $R_5$ are methyl;

$R_6$ is

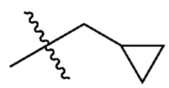

n is 1;

W is C—$R_7$;

$R_7$ is selected from the group consisting of hydrogen and halogen;

$R_8$ and $R_9$ are each independently $C_{1-6}$ alkyl.

In another preferred embodiment, the compound is selected from the group consisting of:
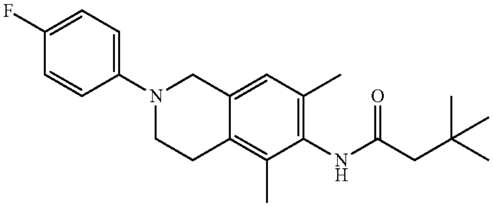
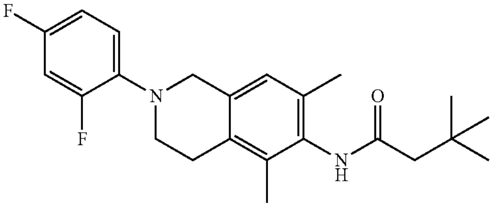
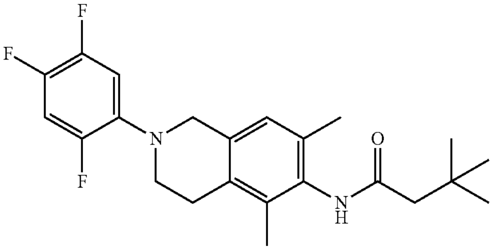
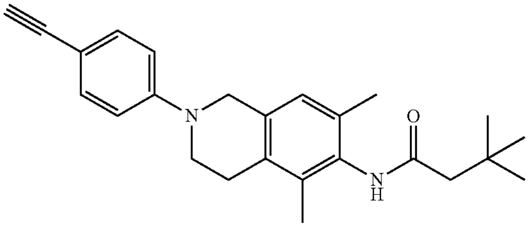
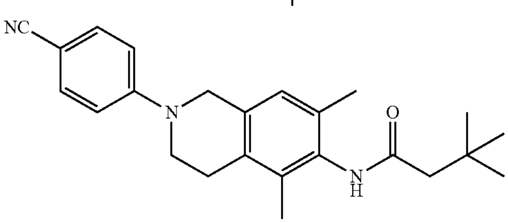
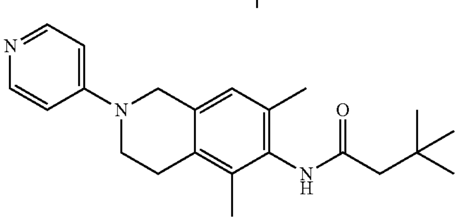
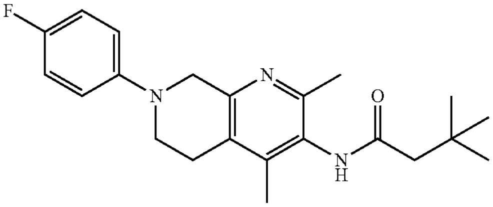
-continued
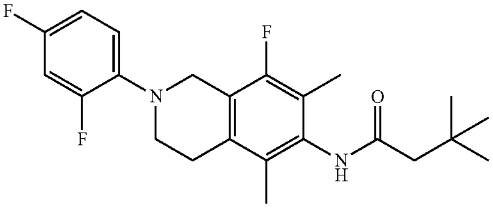
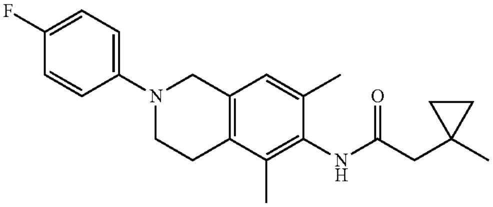
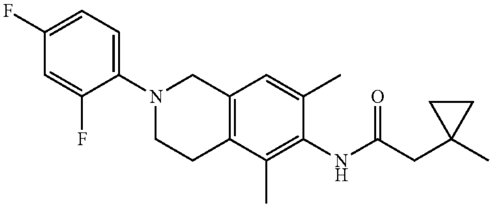
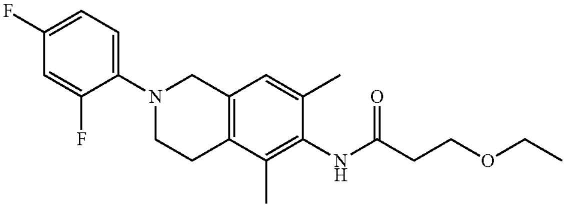
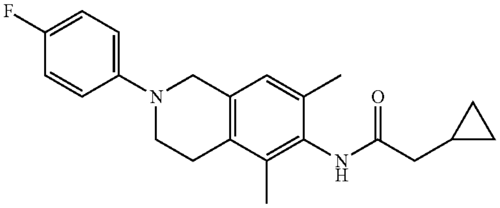
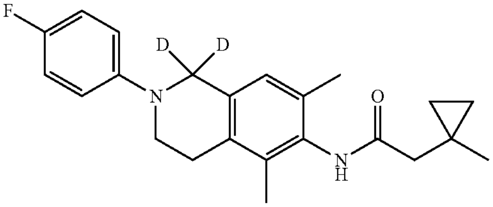
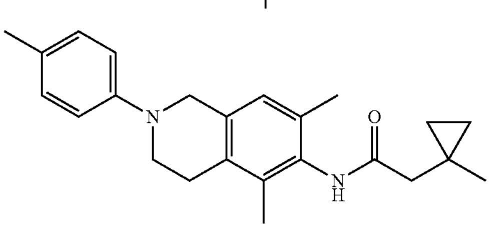
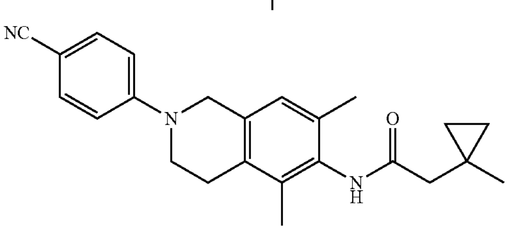

-continued
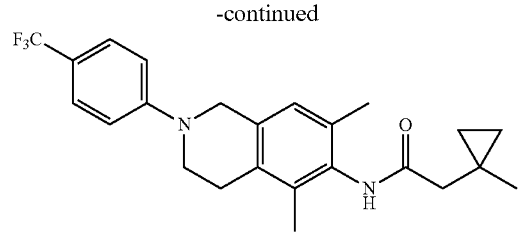
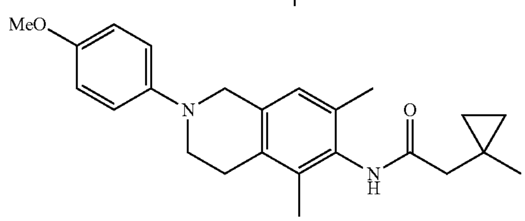
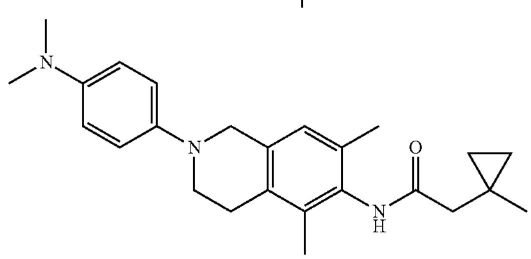
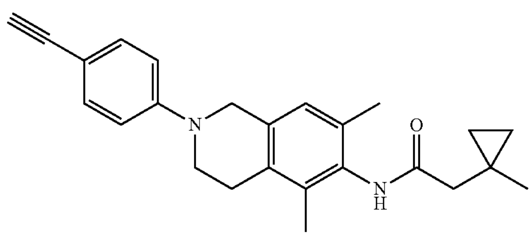
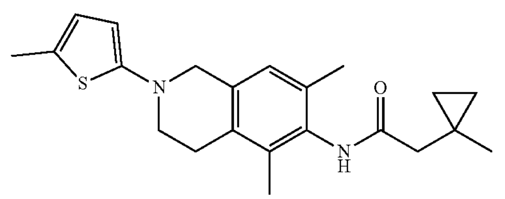
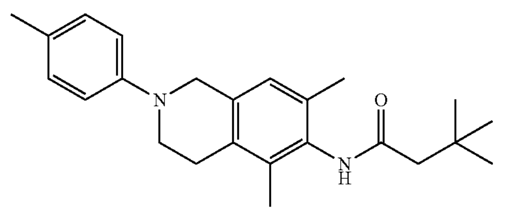
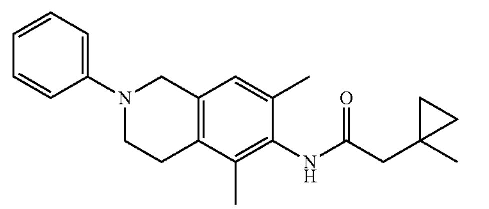
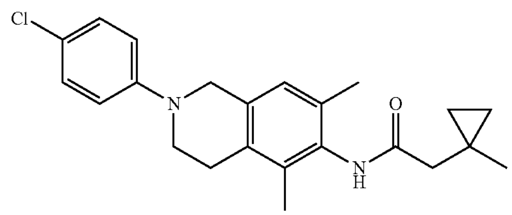
-continued
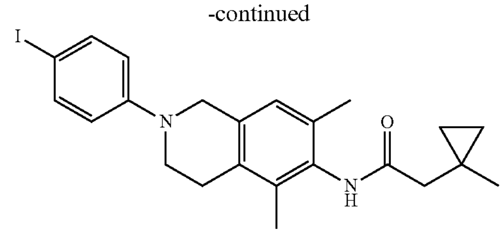
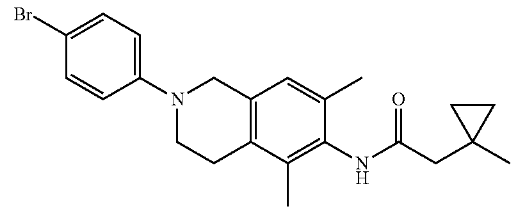
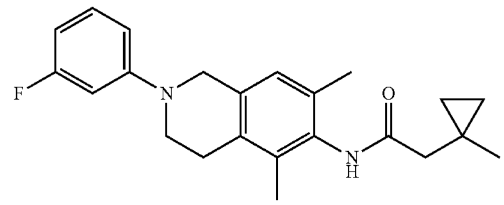
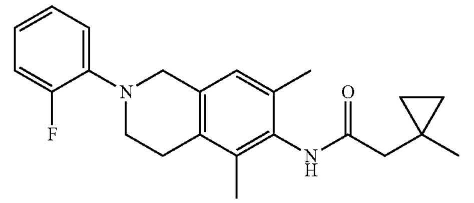
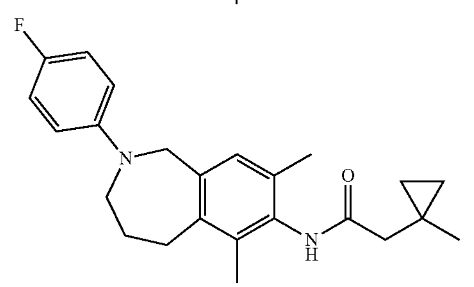
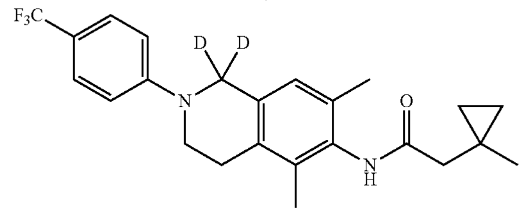
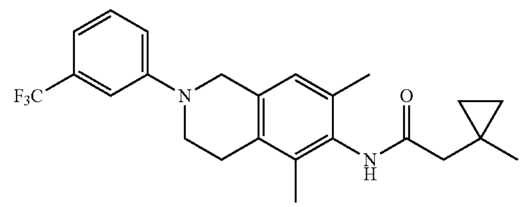
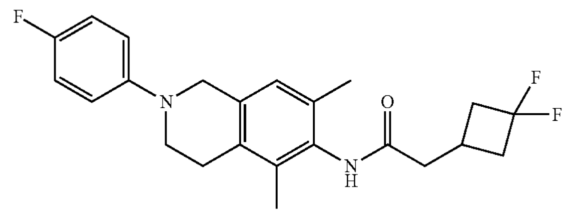

-continued

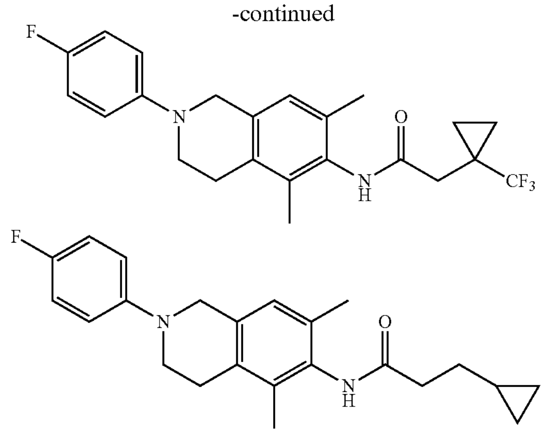

In the second aspect of the present invention, it provides a preparation method of the compound according to the first aspect of the invention or the pharmaceutically acceptable salt, comprising the steps:

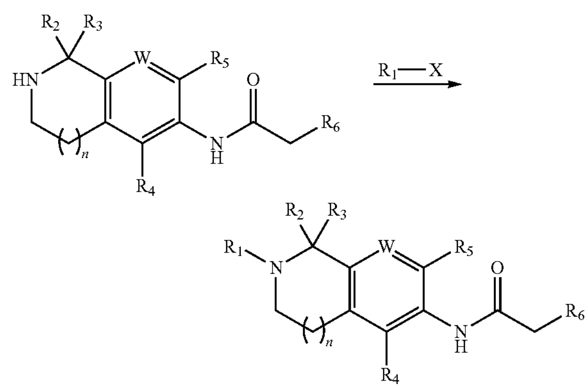

wherein:

X is selected from the group consisting of halogen, —$B(OH)_2$, and —OTf;

$R_1$, $R_2$, $R_3$, $R_4$, $R_5$, $R_6$, n and W are as defined in the first aspect of the invention.

In the third aspect of the present invention, it provides a pharmaceutical composition comprising one or more pharmaceutically acceptable carriers and a therapeutically effective amount of one or more of the compounds according to the first aspect of the present invention or the pharmaceutically acceptable salts thereof.

In the fourth aspect of the present invention, it provides a use of the compound according to the first aspect of the present invention or the pharmaceutically acceptable salt thereof for the preparation of a medicament for the prevention and/or treatment of a disease sensitive to potassium ion channels.

In another preferred embodiment, the disease sensitive to potassium ion channels is a central nervous system disease.

In another preferred embodiment, the central nervous system disease is selected from the group consisting of epilepsy, convulsions, inflammatory pain, neuropathic pain, migraine, depression, anxiety disorder, stroke, Alzheimer's disease, neurodegenerative disease, cocaine abuse, nicotine withdrawal, alcohol withdrawal and tinnitus.

It should be understood that in the present invention, any of the technical features specifically described above and below (such as in the Examples) can be combined with each other so as to constitute new or preferred technical solutions, which will not redundantly be described one by one herein.

DETAILED DESCRIPTION OF THE INVENTION

After long-term and in-depth research, the present inventors unexpectedly prepared a compound represented by formula A with excellent potassium channel opening activity, pharmacokinetics (such as cerebral blood ratio performance, etc.), in vivo efficacy, safety and novel structure through structural optimization. On this basis, the inventors have completed the present invention.

Terms

In the present invention, unless specifically indicated, the terms used have the general meaning well known to those skilled in the art.

In the present invention, the term "halogen" refers to F, Cl, Br or I.

In the present invention, "C1-C6 alkyl" refers to a linear or branched alkyl including 1-6 carbon atoms, such as methyl, ethyl, propyl, isopropyl, butyl, isobutyl, tert-butyl, neopentyl, tert-pentyl, or similar groups.

In the present invention, the term "C2-C6 alkenyl" refers to a straight or branched chain alkenyl having 2-6 carbon atoms containing a double bond, including but not limited to vinyl, propenyl, butenyl, isobutenyl, pentenyl and hexenyl etc.

In the present invention, the term "C2-C6 alkynyl" refers to a straight or branched alkynyl having 2-6 carbon atoms containing a triple bond, including but not limited to ethynyl, propynyl, butynyl, isobutynyl, pentynyl and hexynyl, etc.

In the present invention, the term "C3-C8 cycloalkyl" refers to a cyclic alkyl having 3-8 carbon atoms in the ring, including but not limited to cyclopropyl, cyclobutyl, cyclopentyl, cyclohexyl, cycloheptyl, cyclooctyl, etc. The terms "C3-C6 cycloalkyl" and "C3-C10 cycloalkyl" have similar meanings.

In the present invention, the term "C1-C6 alkoxy" refers to a straight or branched alkoxy having 1-6 carbon atoms, including but not limited to methoxy, ethoxy, propoxy, isopropoxy and butoxy, etc. Preferably C1-C4 alkoxy.

In the present invention, the term "aromatic ring" or "aryl" has the same meaning, preferably "C6-C10 aryl". The term "C6-C10 aryl" refers to an aromatic ring having 6-10 carbon atoms in the ring that does not contain heteroatoms, such as phenyl, naphthyl and the like. The terms "$C_{6-10}$ aryl" and "C6-C10 aryl" have the same meaning, and other similar terms have similar similarities.

In the present invention, the term "aromatic heterocycle" or "heteroaryl" has the same meaning and refers to a heteroaromatic group containing one to more heteroatoms. For example, "C3-C10 heteroaryl" means an aromatic heterocycle containing 1 to 4 heteroatoms selected from the group consisting of oxygen, sulfur and nitrogen and 3-10 carbon atoms.

Non-limiting examples include: furyl, thienyl, pyridyl, pyrazolyl, pyrrolyl, N-alkylpyrrolyl, pyrimidinyl, pyrazinyl, imidazolyl, tetrazolyl and the like. The heteroaryl ring may be fused to an aryl, heterocyclyl or cycloalkyl ring, wherein the ring connected to the parent structure is a heteroaryl ring. Heteroaryl can be optionally substituted or unsubstituted.

In the present invention, the term "halogenated" means substituted by halogen.

In the present invention, the term "substituted" means that one or more hydrogen atoms on a specific group are replaced with a specific substituent. The specific substituents are the substituents described correspondingly in the foregoing, or the substituents appearing in the respective examples. Unless otherwise specified, a substituted group may have a substituent selected from a specific group at any substitutable position of the group, and the substituent may be the same or different at each position. Those skilled in the art will understand that the combinations of substituents contemplated by the present invention are those that are stable or chemically achievable. The substituents are, for example (but not limited to): halogen, hydroxyl, carboxyl (—COOH), C1-C6 alkyl, C2-C6 alkenyl, C2-C6 alkynyl, C3-C8 cycloalkyl, 3-12 membered heterocyclyl, aryl, heteroaryl, C1-C8 aldehyde group, C2-C10 acyl, C2-C10 ester group, amino, C1-C6 alkoxy, C1-C10 sulfonyl and the like.

In the present invention, the term "multiple" independently refers to 2, 3, 4, 5 or 6.

In the present invention, the terms 1-6 refer to 1, 2, 3, 4, 5 or 6. Other similar terms have similar meanings.

Compound

The invention provides a compound shown in formula A or a pharmaceutically acceptable salt thereof, formula A

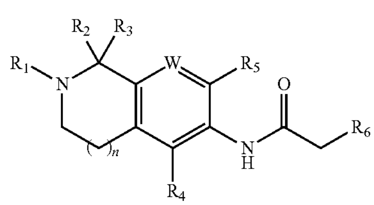

$R_1$, $R_2$, $R_3$, $R_4$, $R_5$, $R_5$, n and W are as defined above.

In another preferred embodiment, in the compound, any one of $R_1$, $R_2$, $R_3$, $R_4$, $R_5$, $R_6$, n and W is a corresponding group in the specific compound.

As used herein, the term "pharmaceutically acceptable salt" refers to a salt formed by a compound of the present invention with an acid or base suitable for use as a medicine. Pharmaceutically acceptable salts include inorganic salts and organic salts. A preferred class of salts is the salts of the compounds of the invention formed with acids. Suitable acids for forming salts include, but are not limited to inorganic acids such as hydrochloric acid, hydrobromic acid, hydrofluoric acid, sulfuric acid, nitric acid, phosphoric acid; organic acids such as formic acid, acetic acid, trifluoroacetic acid, propionic acid, oxalic acid, malonic acid, succinic acid, fumaric acid, maleic acid, lactic acid, malic acid, tartaric acid, citric acid, picric acid, benzoic acid, methylsulfonic acid, ethanesulfonic acid, p-toluenesulfonic acid, benzenesulfonic acid, naphthalenesulfonic acid; and amino acids such as proline, phenylalanine, aspartic acid and glutamic acid.

Another preferred class of salts are salts of the compounds of the invention formed with bases, such as alkali metal salts (such as sodium or potassium salts), alkaline earth metal salts (such as magnesium or calcium salts), ammonium salts (such as lower grades alkanol ammonium salts and other pharmaceutically acceptable amine salts), such as methylamine salt, ethylamine salt, propylamine salt, dimethylamine salt, trimethylamine salt, diethylamine salt, triethylamine salt, tert-butylamine salt, ethylenediamine salt, hydroxyethylamine salt, dihydroxyethylamine salt, trishydroxyethylamine salt, and an amine salt formed from morpholine, piperazine, and lysine, respectively.

Preparation Method

The preparation method of the compound of formula A according to the present invention is more specifically described below, but these specific methods do not constitute any limitation. The compounds of the present invention may also be conveniently prepared by optionally combining various synthetic methods described in the specification or known in the art, and such combinations are readily made by those skilled in the art to which the present invention pertains.

Typically, the preparation process of the compounds of the present invention is as follows, wherein the starting materials and reagents used are commercially available unless otherwise specified.

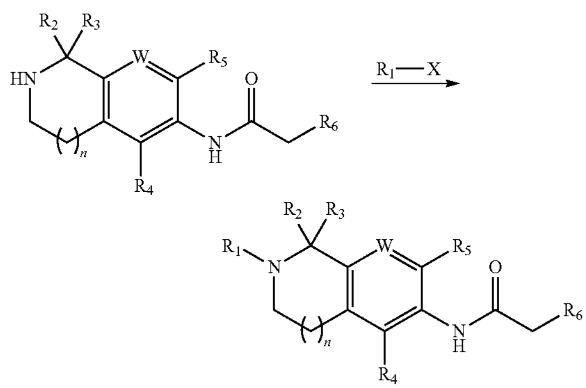

wherein:

X is selected from the group consisting of halogen, —$B(OH)_2$ and —OTf;

$R_1$, $R_2$, $R_3$, $R_4$, $R_5$, $R_6$, n and W are as defined above.

Pharmaceutical Composition and Method for Administration

The pharmaceutical composition of the present invention comprises a safe and effective amount of a compound of the present invention or a pharmacologically acceptable salt thereof, and a pharmacologically acceptable excipient or carrier. In which, "safe and effective amount" is meant that the amount of the compound is sufficient to significantly improve the condition without causing serious side effects. Generally, the pharmaceutical composition contains 1-2000 mg of the compound of the present invention/dose, more preferably, 5-1000 mg of the compound of the present invention/dose. Preferably, the "dose" is a capsule or tablet.

"Pharmaceutically acceptable carrier" means one or more compatible solid or liquid fillers or gelatinous materials which are suitable for human use and should be of sufficient purity and sufficiently low toxicity. "Compatibility" means that each component in the composition can be admixed with the compounds of the present invention and with each other without significantly reducing the efficacy of the compounds. Some examples of pharmaceutically acceptable carriers include cellulose and the derivatives thereof (such as sodium carboxymethyl cellulose, sodium ethyl cellulose, cellulose acetate, etc.), gelatin, talc, solid lubricants (such as stearic acid, magnesium stearate), calcium sulfate, vegetable oils (such as soybean oil, sesame oil, peanut oil, olive oil, etc.), polyols (such as propylene glycol, glycerol, mannitol, sorbitol, etc.), emulsifiers (such as Tween®), wetting agent (such as sodium dodecyl sulfate), coloring agents, flavoring agents, stabilizers, antioxidants, preservatives, pyrogen-free water, etc.

The pharmaceutical composition is an injection, a capsule, a tablet, a pill, a powder, or a granule.

The administration mode of the compound or pharmaceutical composition of the present invention is not particularly limited, and representative administration modes include, but are not limited to, oral, intratumoral, rectal, parenteral (intravenous, intramuscular or subcutaneous) and topical administration.

Solid dosage forms for oral administration include capsules, tablets, pills, powders and granules. In these solid dosage forms, the active ingredient is mixed with at least one conventional inert excipient (or carrier), such as sodium citrate or dicalcium phosphate, or mixed with any of the following components: (a) fillers or compatibilizer, such as starch, lactose, sucrose, glucose, mannitol and silicic acid: (b) binders, such as hydroxymethyl cellulose, alginate, gelatin, polyvinylpyrrolidone, sucrose and arabic gum; (c) humectants, such as glycerol; (d) disintegrating agents such as agar, calcium carbonate, potato starch or tapioca starch, alginic acid, certain composite silicates, and sodium carbonate; (e) retarding solvents, such as wax, (f) absorption accelerators, such as quaternary ammonium compound; (g) wetting agents, such as cetyl alcohol and glyceryl monostearate; (h) adsorbents, such as kaolin; and (i) lubricants, such as talc, calcium stearate, magnesium stearate, solid polyethylene glycol, sodium dodecyl sulfate or mixture thereof. In capsules, tablets and pills, the dosage forms may also contain buffering agents.

Solid dosage forms such as tablets, dragees, capsules, pills and granules can be prepared with coatings and shells such as enteric coatings and other materials known in the art. They may contain opacifying agents and the release of the active compound or compound in such compositions may be released in a portion of the digestive tract in a delayed manner. Examples of embedding components that can be employed are polymeric materials and waxy materials. If necessary, the active compound may also be in microencapsulated form with one or more of the above-mentioned excipients.

Liquid dosage forms for oral administration include pharmaceutically acceptable emulsions, solutions, suspensions, syrups or tinctures. In addition to the active compound, the liquid dosage form may contain inert diluents conventionally used in the art, such as water or other solvents, solubilizers and emulsifiers, such as ethanol, isopropanol, ethyl carbonate, ethyl acetate, propylene glycol, 1,3-butanediol, dimethylformamide and oils, especially cottonseed oil, peanut oil, corn germ oil, olive oil, castor oil and sesame oil or mixtures of these substances.

In addition to these inert diluents, the compositions may contain adjuvants such as wetting agents, emulsifying and suspending agents, sweetening agents, flavoring agents and spices.

In addition to the active compound, the suspension may contain suspending agent, such as ethoxylated isooctadecanol, polyoxyethylene sorbitol and dehydrated sorbitan ester, microcrystalline cellulose, aluminum methoxide and agar, or the mixture thereof etc.

The compositions for parenteral injection may comprise physiologically acceptable sterile aqueous or anhydrous solutions, dispersions, suspensions or emulsions, and sterile powders which can be re-dissolved into sterile injectable solutions or dispersions. Suitable aqueous and non-aqueous carriers, diluents, solvents or excipients include water, ethanol, polyols and any suitable mixtures thereof.

Dosage forms for the compounds of the invention for topical administration include ointments, powders, patches, sprays and inhalants. The active ingredient is mixed under sterile conditions with a physiologically acceptable carrier and any preservatives, buffers, or propellants which may be required if necessary.

The compounds of the invention can be administered alone or in combination with other pharmaceutically acceptable compounds.

The treatment method of the present invention can be administered alone or in combination with other treatment means or therapeutic drugs.

When the pharmaceutical composition is used, a safe and effective amount of the compound of the present invention is administered to a mammal (such as a human) in need of treatment, wherein the dosage at the time of administration is the pharmaceutically effective dosage, for people having a body weight of 60 kg, the daily dose is usually 1~2000 mg, preferably 5~1000 mg. Of course, specific doses should also consider factors such as the administration route, the health of the patient, etc., which are within the skill of the skilled physician.

Compared with the prior art, the present invention has the following main advantages:

(1) the compound has better pharmacokinetic properties, such as better cerebral blood ratio, half-life, exposure, metabolic stability and other properties;

(2) the compound has better potassium ion channel opening activity, better ion channel selectivity, better in vivo efficacy and better safety;

(3) the compound is expected to be used for the treatment and/or prevention of diseases and conditions affected by the activity of potassium ion channels.

The present invention will be further illustrated below with reference to the specific examples. It should be understood that these examples are only to illustrate the invention but not to limit the scope of the invention. Experimental methods in which the specific conditions are not specified in the following examples are usually in accordance with conventional conditions such as the conditions described in Sambrook et al., Molecular Cloning: Laboratory Manual (New York: Cold Spring Harbor Laboratory Press, 1989), or in accordance with the conditions recommended by the manufacturer. Unless indicated otherwise, percentage and parts are calculated by weight.

Unless otherwise defined, all professional and scientific terminology used in the text have the same meanings as known to the skilled in the art. In addition, any methods and materials similar or equal with the recorded content can apply to the methods of the invention. The method of the preferred embodiment described herein and the material are only for demonstration purposes.

The experimental materials and reagents used in the following examples can be obtained from commercial sources unless otherwise specified.

Example 1 Preparation of Compound A

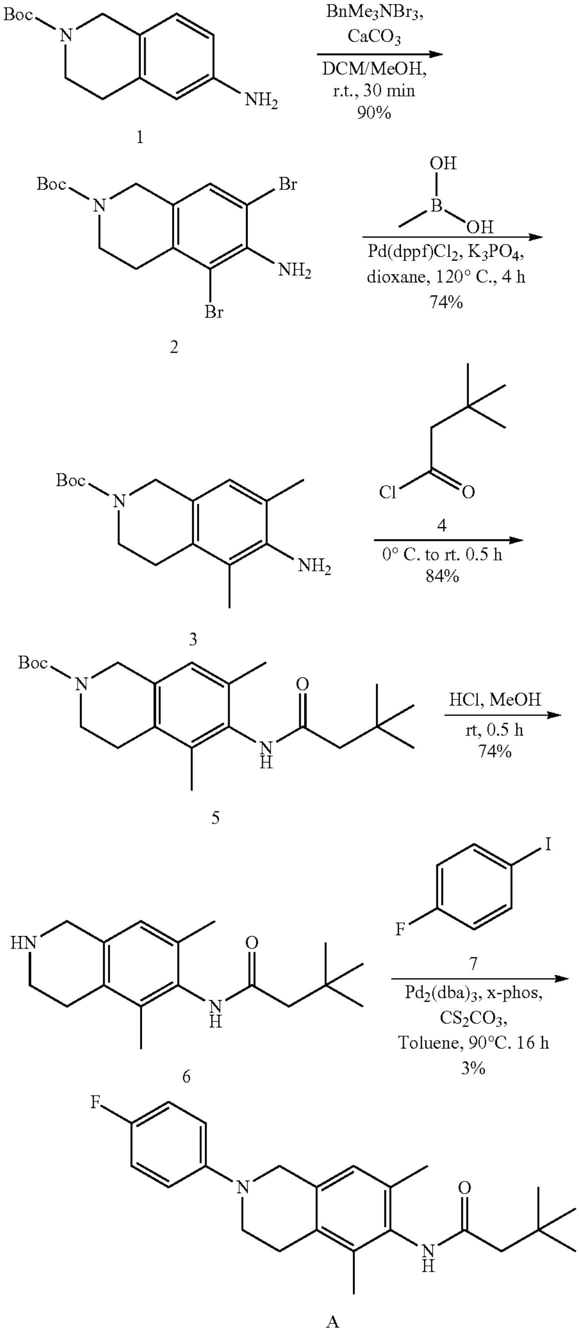

1, 2, 3, 4, 5, 6, 7, A

Step 1. Compound 2

Compound 1 (2 g, 8.05 mmol, 1.0 eq) was dissolved in a mixed solvent of dichloromethane (100 mL) and methanol (10 mL), then $BnMe_3NBr_3$ (6.28 g, 16.1 mmol, 2.0 eq) and calcium carbonate (2.01 g, 20.1 mmol, 2.5 eq) were added, and the reaction solution was stirred at room temperature for 0.5 h. The reaction solution was filtered and the filtrate was concentrated to obtain the residue which was purified by neutral alumina column chromatography (petroleum ether: ethyl acetate=15:1) to obtain compound 2 (2.9 g, yield 90%) as a white solid.

LCMS: $[M+H]^+$=406.9.

Step 2. Compound 3

Compound 2 (1 g, 2.46 mmol, 1.0 eq) was dissolved in 1,4-dioxane (50 mL), then methyl boric acid (589 mg, 9.84 mmol, 4.0 eq), potassium phosphate (2.089 g, 9.84 mmol, 4.0 eq) and $Pd(dppf)Cl_2$ (0.1 g, 0.14 mmol, 0.06 eq) were added, and the reaction solution was heated to 120° C. under nitrogen protection and stirred for 4 hours. After cooling to room temperature, the reaction solution was filtered, the filtrate was diluted with water, and then extracted with ethyl acetate (3×40 mL), the organic phase was washed with saturated sodium chloride solution, dried over anhydrous sodium sulfate, and concentrated to obtain the residue which was purified by silica gel column chromatography (petroleum ether:ethyl acetate=10:1) to obtain compound 3 (504 mg, yield 74%) as a white solid.

LCMS: $[M+H]^+$=277.2.

Step 3. Compound 5

Compound 3 (600 mg, 2.17 mmol, 1.0 eq) was dissolved in dichloromethane (15 mL), cooled to 0° C., triethylamine (0.78 mL, 5.43 mmol, 2.5 eq) and compound 4 (438 mg, 3.26 mmol, 1.5 eq) were added, and the reaction solution was raised to room temperature and stirred for 0.5 h. The reaction solution was diluted with water, then extracted with dichloromethane (3×10 mL), the organic phase was washed with saturated sodium chloride solution, dried over anhydrous sodium sulfate and concentrated, and the residue was slurried and purified with mixed solvent (petroleum ether/ethyl acetate=30 mL/3 mL) for half an hour, then filtered, and the obtained solid was dried to obtain compound 5 (680 mg, yield 84%) as a white solid.

Step 4. Compound 6

Compound 5 (680 mg, 1.82 mmol, 1.0 eq) and methanol hydrochloride solution (4M, 13 mL) were added to a single-neck flask, and stirred at room temperature for 0.5 h. The reaction solution was concentrated and diluted with ethyl acetate (10 mL), then washed with sodium carbonate aqueous solution (0.5 M, 20 mL), and the separated aqueous phase was extracted with ethyl acetate (3×10 mL). The combined organic phase was washed with saturated sodium chloride solution, dried over anhydrous sodium sulfate, and concentrated the organic layer to obtain the residue which was dissolved in tetrahydrofuran, dried over anhydrous sodium sulfate, and concentrated to obtain compound 6 (370 mg, yield 74%) as a white solid.

LCMS: $[M+H]^+$=275.2

Step 5. Compound A

Compound 6 (150 mg, 0.547 mmol, 1.5 eq) was dissolved in toluene (50 mL), and then cesium carbonate (237 mg, 0.728 mmol, 2.0 eq), X-Phos (35 mg, 0.0728 mmol, 0.2 eq), compound 7 (81 mg, 0.364 mmol, 1.0 eq) and $Pd_2(dba)_3$ (34 mg, 0.0364 mmol, 0.1 eq) were sequentially added, and the reaction solution was stirred at 90° C. for 16 hours under the protection of nitrogen. The reaction solution was cooled to room temperature and filtered, the filtrate was diluted with water, and then extracted with ethyl acetate (3×20 mL), the organic phase was washed with saturated sodium chloride solution, dried over anhydrous sodium sulfate, and concentrated to obtain the residue which was purified by silica gel column chromatography (petroleum ether:ethyl acetate=2:1) to obtain compound A (6.0 mg, 3%) as a white solid.

LCMS: $[M+H]^+$=369.2

$^1H$ NMR (400 MHz, DMSO) δ 9.10 (s, 1H), 7.08-7.02 (m, 4H), 6.90 (s, 1H), 4.26 (s, 2H), 3.49 (s, 2H), 2.74-2.71 (m, 2H), 2.21 (s, 2H), 2.11 (s, 3H), 2.01 (s, 3H), 1.06 (s, 9H).

Example 2 Preparation of Compound B

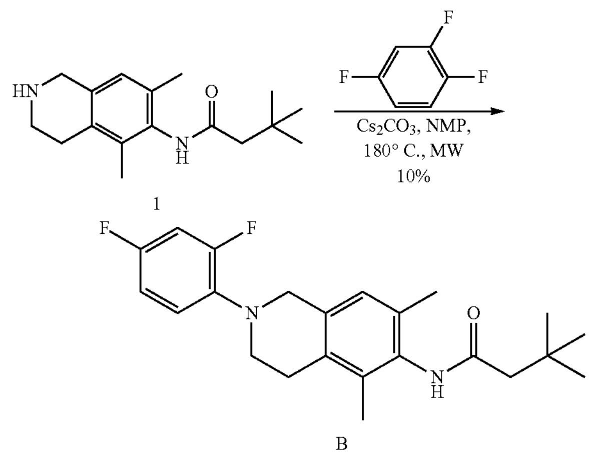

1

B

Step 1. Compound B

Compound 1 (600 mg, 2.19 mmol, 1.0 eq), compound 2 (3.6 g, 27.3 mmol, 12.4 eq) and cesium carbonate (7.14 g, 21.9 mmol, 10 eq) were added to N-methylpyrrolidone (60 mL), the reaction solution was heated to 180° C. in a microwave reactor and stirred for 4 hours. The reaction solution was cooled to room temperature and diluted with ethyl acetate (150 mL), then washed with saturated sodium chloride solution (80 mL×4), dried over anhydrous sodium sulfate and concentrated, and the resulting residue was purified by silica gel column chromatography (petroleum ether/ethyl acetate=10/1) to obtain compound B (83.9 mg, yield 10%) as a white solid.

LCMS: $[M+H]^+$=387.1

$^1H$ NMR (400 MHz, DMSO-$d_6$) δ 9.11 (s, 1H), 7.21-7.15 (m, 1H), 6.94-6.84 (m, 2H), 6.80-6.69 (m, 1H), 4.19 (s, 2H), 3.44-3.36 (m, 2H), 2.76-2.71 (m, 2H), 2.21 (s, 2H), 2.10 (s, 3H), 2.01 (s, 3H), 1.05 (s, 9H).

Example 3 Preparation of Compound C

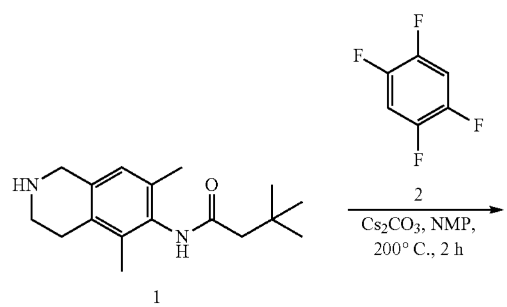

1

-continued

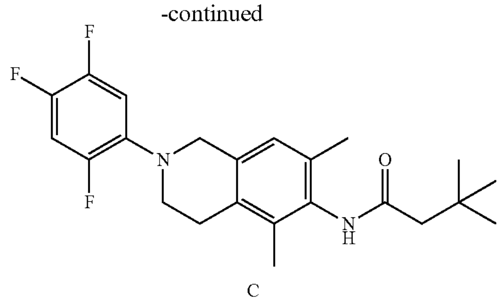

C

Step 1. Compound C

Compound 1 (100 mg, 0.36 mmol, 1.0 eq) was dissolved in N-methylpyrrolidone (5 mL), then cesium carbonate (1.0 g, 3.1 mmol, 8.6 eq) and compound 2 (1.0 g, 6.67 mmol, 18.5 eq) were added. The reaction solution was heated to 200° C. in a microwave reactor and stirred for 2 hours, cooled to room temperature and filtered, and the solid was washed with ethyl acetate (3×5 mL), and the filtrate was washed with saturated sodium chloride solution (3×10 mL). The organic phase was dried over anhydrous sodium sulfate and concentrated to obtain the residue which was purified by silica gel column chromatography (petroleum ether/ethyl acetate=2/1) to obtain compound C (15.5 mg, yield 10%) as a white solid.

LCMS: $[M+H]^+$=405.1

$^1H$ NMR (400 MHz, DMSO-$d_6$) δ 9.13 (s, 1H), 7.58-7.46 (m, 1H), 7.23-7.16 (m, 1H), 6.86 (s, 1H), 4.15 (s, 2H), 3.37-3.33 (m, 2H), 2.79-2.72 (m, 2H), 2.22 (s, 2H), 2.11 (s, 3H), 2.02 (s, 3H), 1.07 (s, 9H).

Example 4 Preparation of Compound D

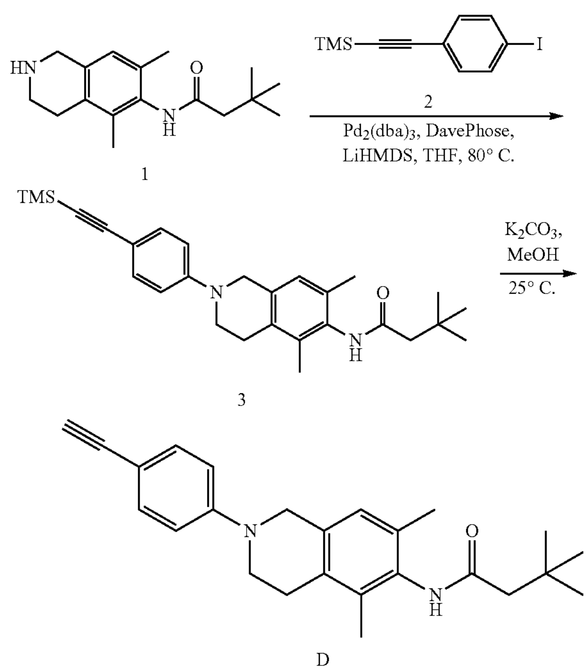

1

3

D

Step 1. Compound 3

Compound 1 (50 mg, 0.182 mmol, 1.0 eq) was dissolved in tetrahydrofuran (5 mL), and then compound 2 (164 mg, 0.547 mmol, 3.0 eq), $Pd_2(dba)_3$ (17 mg, 0.018 mmol, 0.1 eq), Dave-Phos (14 mg, 0.036 mmol, 0.2 eq) and LiHMDS (1 M, 1.8 mL, 1.8 mmol, 10 eq) were sequentially added. The reaction solution was stirred at 80° C. under nitrogen protection for 2 hours, cooled to room temperature, diluted with ethyl acetate (150 mL), and then washed with saturated sodium chloride solution (80 mL×4). The obtained organic phase was dried over anhydrous sodium sulfate and then concentrated. The obtained residue was purified by silica gel column chromatography (petroleum ether/ethyl acetate=3/1) to obtain compound 3 (46 mg, yield 28%) as a yellow solid.

LCMS: $[M+H]^+$=447.2

Step 2. Compound D

Compound 3 (20 mg, 0.045 mmol, 1.0 eq) and potassium carbonate (62 mg, 0,447 mmol, 10 eq) were added to methanol (3 mL), and the reaction solution was stirred at 25° C. for 2 hours. The reaction solution was concentrated, the resulting residue was dissolved in ethyl acetate (20 mL), and then washed with saturated sodium chloride solution (10 mL×2), the resulting organic phase was dried over anhydrous sodium sulfate and concentrated, and the residue was purified by pre-HPLC (0.1% formic acid/acetonitrile/water) to obtain compound D (4.2 mg, yield 7%) as a reddish solid.

LCMS: $[M+H]^+$=375.2

$^1$H NMR (400 MHz, DMSO-$d_6$) δ 9.11 (s, 1H), 7.31 (d, J=8.8 Hz, 2H), 7.03-6.88 (m, 3H), 4.38 (s, 2H), 3.90 (s, 1H), 3.61 (s, 2H), 2.75-2.72 (m, 2H), 2.21 (s, 2H), 2.10 (s, 3H), 2.02 (s, 3H), 1.06 (s, 9H).

Example 5 Preparation of Compound E

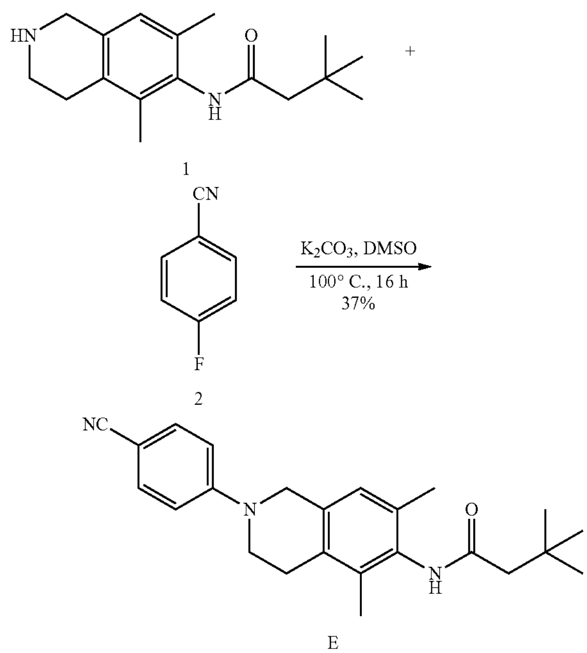

1

2

E

Step 1. Compound E

Compound 1 (100 mg, 0.36 mmol, 1.0 eq) was dissolved in dimethyl sulfoxide (2 mL), then compound 2 (66 mg, 0.55 mmol, 1.5 eq) and potassium carbonate (151 mg, 1.09 mmol, 3.0 eq) were added sequentially, and the reaction solution was stirred at 100° C. for 16 hours. After cooling to room temperature, water (20 mL) was added to the reaction solution, and extracted with ethyl acetate (3×20 mL). The combined organic phase was washed with saturated sodium chloride solution and dried over anhydrous sodium sulfate. The residue obtained after concentration was purified by silica gel column chromatography (dichloromethane/methanol=50/1) to obtain compound E (50.3 mg, yield 37%) as a white solid.

LCMS: $[M+H]^+$=376.2

$^1$H NMR (400 MHz, DMSO-$d_6$) δ 9.13 (s, 1H), 7.60-7.57 (m, 2H), 7.08-7.05 (m, 2H), 6.94 (s, 1H), 4.49 (s, 2H), 3.69 (s, 2H), 2.77 (t, J=5.6 Hz, 2H), 2.21 (s, 2H), 2.11 (s, 3H), 2.03 (s, 3H), 1.06 (s, 9H).

Example 6 Preparation of Compound F

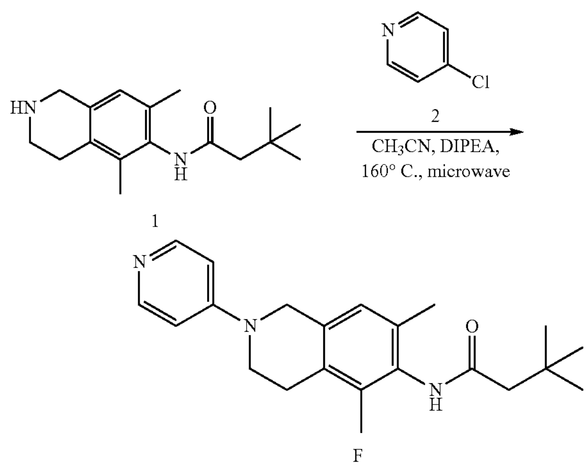

2

1

F

Step 1. Compound F

Compound 1 (120 mg, 0.44 mmol, 1.0 eq) was dissolved in acetonitrile (20 mL), compound 2 (148 mg, 1.31 mmol, 3.0 eq) and diisopropylethylamine (339 mg, 2.63 mmol, 6.0 eq) were added, and heated in a microwave reactor to 160° C., and reacted for 1 hour. The reaction solution was concentrated after being cooled to room temperature, diluted with water, then extracted with dichloromethane (3×100 mL), the combined organic phase was washed with saturated sodium chloride solution (50 mL), dried over anhydrous sodium sulfate, and the residue obtained after concentration was purified by silica gel column chromatography (dichloromethane/methanol=10/1) to obtain compound F (40 mg, yield 26%) as a yellow solid.

LCMS: $[M+H]^+$=352.2

Example 7 Preparation of Compound G

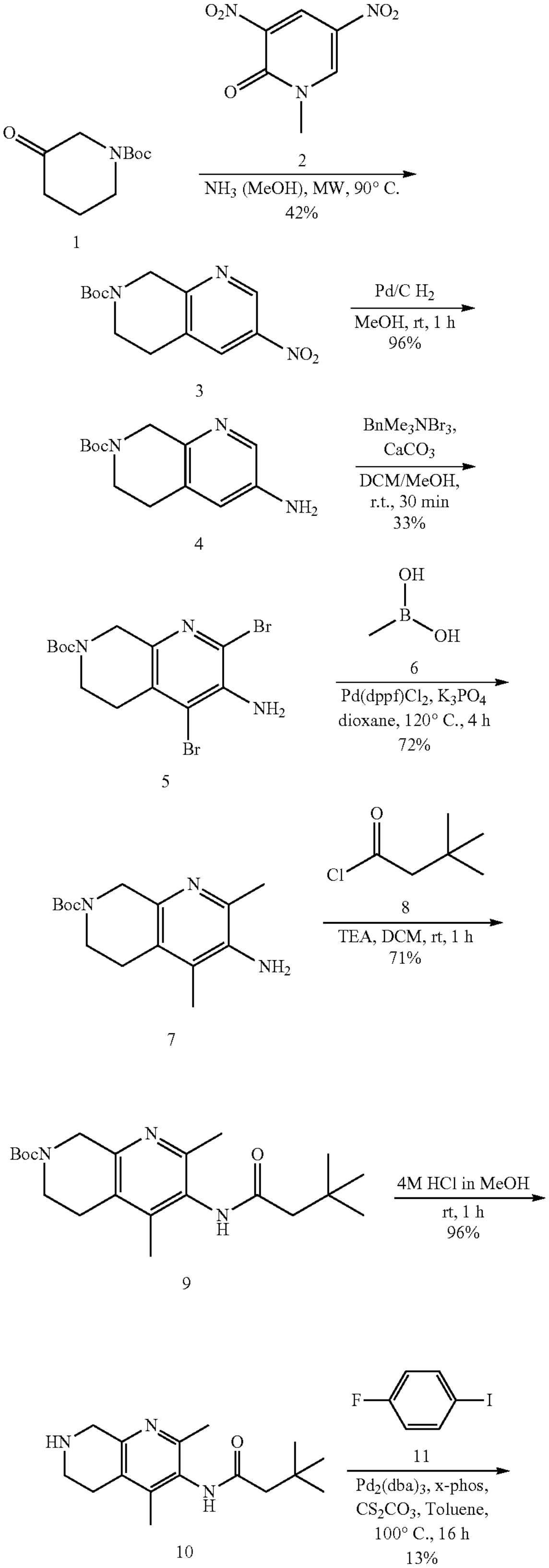

-continued

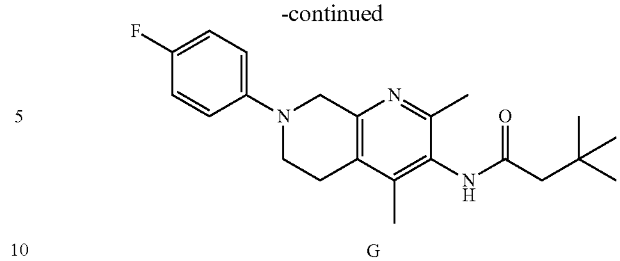

G

Step 1. Compound 3

Compound 1 (600 mg, 3.0 mmol, 1.0 eq) and compound 2 (780 mg, 3.9 mmol, 1.3 eq) were dissolved in a solution of ammonia in methanol (1M, 10.5 mL), and the reaction solution was heated to 90° C. in a microwave reactor and reacted for half an hour. The reaction solution was cooled to room temperature and then concentrated, extracted with ethyl acetate (50 mL×3) and saturated sodium bicarbonate aqueous solution, the organic phases were combined and dried over anhydrous sodium sulfate, and the residue obtained after concentration was purified by silica gel column chromatography (petroleum ether/ethyl acetate=100/15) to obtain compound 3 (350 mg, yield 42%) as a white solid.

Step 2. Compound 4

Compound 3 (350 mg, 1.25 mmol, 1.0 eq) and palladium carbon (10%, 100 mg) were dissolved in methanol (30 mL) and stirred for 1 hour at room temperature under a hydrogen atmosphere of 1 atmosphere. The reaction solution was filtered and the filtrate was concentrated to obtain compound 4 (300 mg, yield 96%) as a colorless oil.

LCMS: $[M+H]^+$=250.1.

Step 3. Compound 5

Compound 4 (300 mg, 1.2 mmol, 1.0 eq), benzyltrimethylammonium tribromide (936 mg, 2.4 mmol, 2.0 eq) and calcium carbonate (300 mg, 3.0 mmol, 2.5 eq) were dissolved in a mixed solvent of dichloromethane/methanol (10/1,40 mL/4 mL) and stirred at room temperature for half an hour. The reaction solution was filtered, and the filtrate was concentrated and purified by silica gel column chromatography (petroleum ether/ethyl acetate=10/1) to obtain compound 5 (160 mg, yield 33%) as a white solid.

LCMS: $[M+Na]^+$=429.9.

Step 4. Compound 7

Compound 5 (160 mg, 0.4 mmol, 1.0 eq) was dissolved in 1,4-dioxane (15 mL), methylboric acid (96 mg, 1.6 mmol, 4.0 eq), $Pd(dppf)Cl_2$ (58 mg, 0.08 mmol, 0.2 eq) and potassium phosphate (339 mg, 1.6 mmol, 4.0 eq) were added. The reaction solution was heated to 120° C. under nitrogen atmosphere and reacted for 4 hours. The reaction solution was cooled to room temperature and filtered. The residue obtained after concentration of the filtrate was purified by silica gel column chromatography (petroleum ether/ethyl acetate=65/35) to obtain compound 7 (80 mg, yield 72%) as a white solid.

LCMS: $[M+H]^+$=278.1

Step 5. Compound 9

Compound 7 (80 mg, 0.3 mmol, 1.0 eq) and triethylamine (116 mg, 0.9 mmol, 3.0 eq) were dissolved in dichloromethane (15 mL), compound 8 (60 mg, 0.45 mmol, 1.5 eq) was slowly added under nitrogen atmosphere, and stirred at room temperature for 1 hour. The reaction solution was extracted with ethyl acetate (50 mL×3) and saturated sodium bicarbonate aqueous solution. The combined organic phase was dried over anhydrous sodium sulfate and concentrated. The residue was purified by silica gel column chromatography (petroleum ether/ethyl acetate=65/35) to obtain compound 9 (80 mg, 71%) as a light yellow solid.

LCMS: $[M+H]^+$=376.3

Step 6. Compound 10

Compound 9 (80 mg, 0.21 mmol, 1.0 eq) was dissolved in a solution of hydrogen chloride in methanol (4 M, 4 mL) and stirred for 1 hour at room temperature. After the reaction solution was concentrated, compound 10 (70 mg, yield 96%) was obtained as a pale yellow oil.

LCMS: $[M+H]^+$=276.2

Step 7. Compound G

Compound 10 (30 mg, 0.11 mmol, 1.0 eq) and compound 11 (38 mg, 0.17 mmol, 1.5 eq) were dissolved in toluene (10 mL), and then $Pd_2(dba)_3$ (20 mg, 0.022 mmol, 0.2 eq), X-Phos (10 mg, 0.022 mmol, 0.2 eq) and cesium carbonate (90 mg, 0.275 mmol, 2.5 eq) were sequentially added, the reaction solution was heated to 100° C. under nitrogen atmosphere and reacted for 16 hours. The reaction solution was cooled to room temperature and then concentrated. The obtained residue was purified by silica gel column chromatography (petroleum ether/ethyl acetate=1/1) to obtain compound G (5.3 mg, yield 13%) as a white solid.

LCMS: $[M+H]^+$=370.1

$^1$H NMR (400 MHz, $CDCl_3$) δ 7.02-6.94 (m, 4H), 6.80 (s, 1H), 4.35 (s, 2H), 3.50 (t, J=5.6 Hz, 2H), 2.84 (t, J=5.6 Hz, 2H), 2.48 (s, 3H), 2.33 (s, 2H), 2.15 (s, 3H), 1.16 (s, 9H).

Example 8 Preparation of Compound H

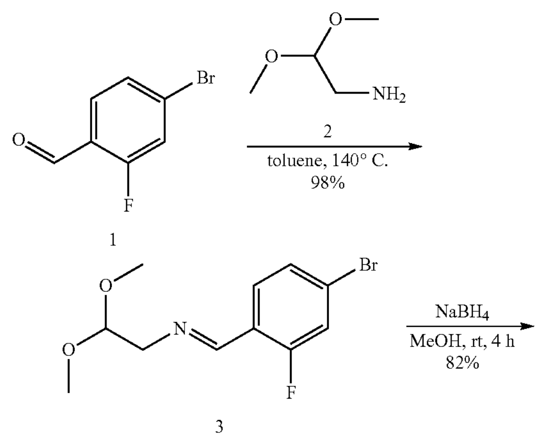

-continued

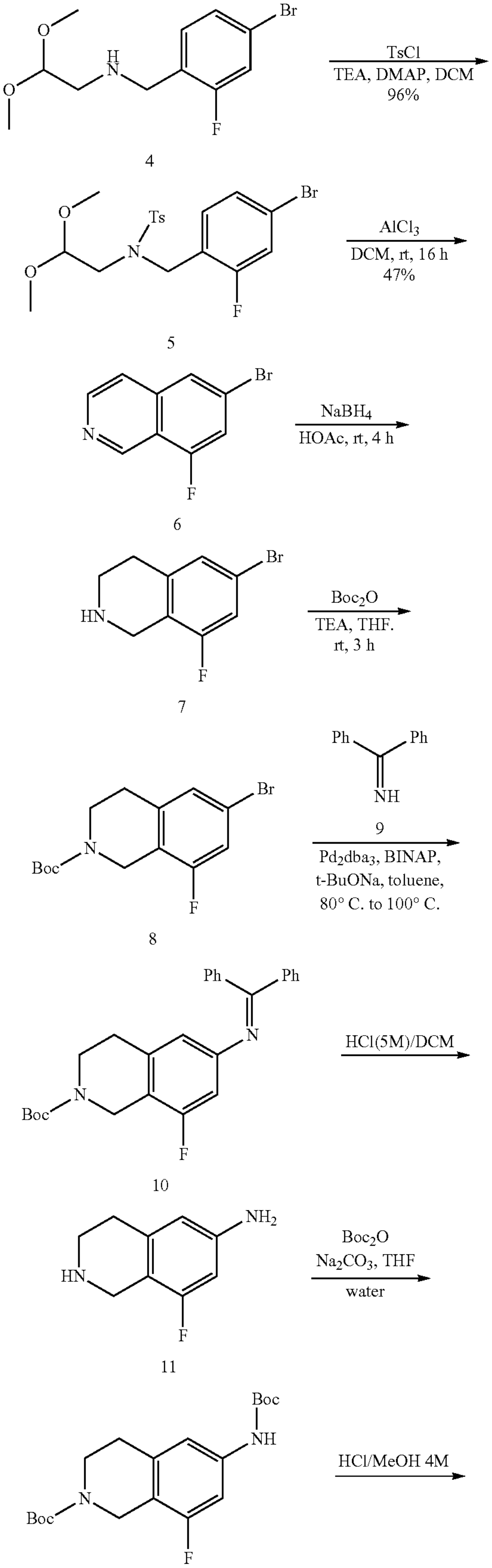

-continued

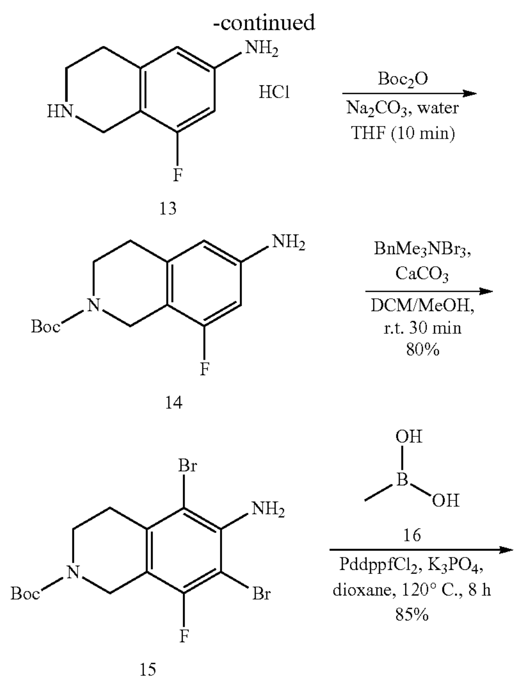

13

14

15

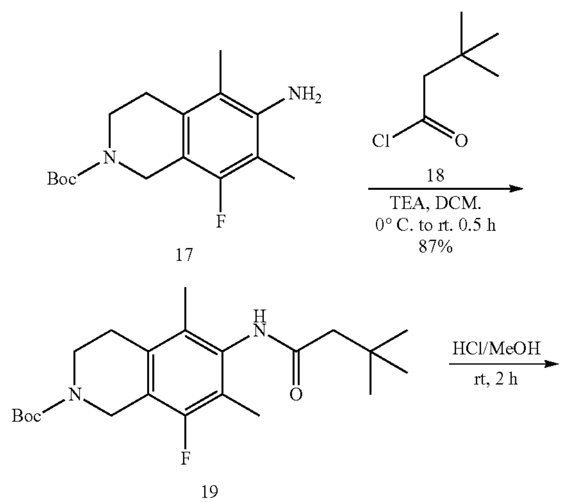

17

19

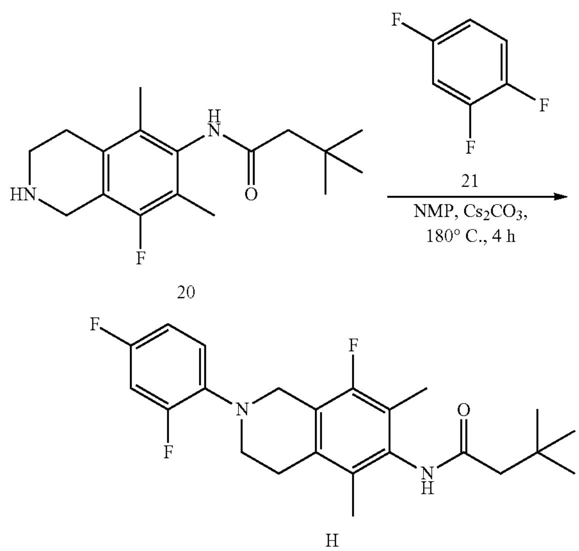

20

H

Step 1. Compound 3

Compound 1 (5.0 g, 24.63 mmol, 1.0 eq) was dissolved in toluene (100 mL), compound 2 (3.88 g, 36.945 mmol, 1.5 eq) was added, and the reaction solution was heated to 140° C. and stirred for 16 hours. After cooling to room temperature, the reaction solution was concentrated to obtain compound 3 (7 g, yield 98%) as a brown oil, which was directly used for the next reaction without purification.

Step 2. Compound 4

Compound 3 (3 g, 10.344 mmol, 1.0 eq) was dissolved in methanol (30 mL), cooled to 0° C., then sodium borohydride (0.27 g, 7.241 mmol, 0.7 eq) was added, the temperature was heated to room temperature, and the reaction solution was stirred for 2 hours. Ice water was added to the reaction solution, methanol was removed by concentration, and ethyl acetate (3×30 mL) was added for extraction. The combined organic phase was washed with saturated sodium chloride solution, dried over anhydrous sodium sulfate, and the residue obtained after concentration was purified by silica gel column chromatography (petroleum ether/ethyl acetate=4/1) to obtain compound 4 (2.5 g, yield 82%) as a white solid.

LCMS: $[M+H]^+$=292.0

Step 3. Compound 5

Compound 4 (7.45 g, 25.5 mmol, 1.0 eq) was dissolved in dichloromethane (200 mL), 4-dimethylaminopyridine (156 mg, 1.28 mmol, 0.05 eq) and triethylamine (5.16 g, 51.0 mmol, 2.0 eq) were sequentially added, the reaction solution was cooled to 0° C. under nitrogen protection, and p-methylbenzenesulfonyl chloride (5.10 g, 26.8 mmol, 1.05 eq) was added. The reaction solution was raised to room temperature and stirred for 16 hours, then quenched with ice water (200 mL), and the aqueous phase was extracted with dichloromethane (200 mL). The separated organic phase was dried over anhydrous sodium sulfate and concentrated. The obtained residue was purified by silica gel column chromatography (petroleum ether:ethyl acetate=10:1) to obtain compound 5 (11.0 g, yield 96%).

LCMS: $[M+Na]^+$=469.9

Step 4. Compound 6

Dichloromethane (300 mL) was added to a reaction flask containing aluminum trichloride (22.0 g, 165 mmol, 6.7 eq), cooled to 0° C. under nitrogen protection, and compound 5 (11.0 g, 24.65 mmol, 1.0 eq) in methylene chloride (100 mL) solution was added. The reaction solution was raised to room temperature and stirred for 16 hours, then quenched with ice water (100 mL), the pH value of the solution was adjusted to be 10 with ammonia water, and the aqueous phase was extracted with dichloromethane (200 mL). The combined organic phase was dried over anhydrous sodium sulfate, and the residue obtained after concentration was purified by silica gel column chromatography (petroleum ether; ethyl acetate=4/1) to obtain compound 6 (2.6 g, yield 47%).

LCMS: $[M+H]^+$=225.9

Step 5. Compound 7

Compound 6 (2.6 g, 11.5 mmol, 1.0 eq) was dissolved in acetic acid (40 mL), and sodium borohydride (1.3 g, 34.5 mmol, 3.0 eq) was added after cooling to 0° C. under nitrogen protection. The reaction solution was raised to room temperature and stirred for 2 hours, diluted with water (200 mL), cooled to 0° C., the pH value of the solution was adjusted to be 10 with sodium carbonate, and then extracted with ethyl acetate (3×200 mL). The combined organic phase was washed with saturated sodium chloride solution, dried over anhydrous sodium sulfate, and concentrated to obtain crude compound 7 (3.0 g), which was directly used for the next reaction without purification.

LCMS: $[M+H]^+$=230.0

Step 6. Compound 8

Compound 7 (3.0 g, 11.5 mmol, 1.0 eq) was dissolved in tetrahydrofuran (40 mL), diisopropylethylamine (743 mg, 5.75 mmol, 0.5 eq) and $Boc_2O$ (3.0 g, 13.8 mmol, 1.2 eq) were added. The reaction solution was stirred at room temperature for 16 hours and then concentrated, and the resulting residue was purified by silica gel column chromatography (petroleum ether:ethyl acetate=10:1) to obtain compound 8 (3.0 g, yield of two-step: 79%).

LCMS: $[M+Na]^+$=352.0

Step 7. Compound 10

Compound 8 (3.0 g, 9.09 mmol, 1.0 eq) and compound 9 (3.3 g, 18.7 mmol, 2.0 eq) were dissolved in toluene (100 mL), and then cesium carbonate (8.88 g, 27.26 mmol, 3.0 eq), BINAP (1.13 g, 1.82 mmol, 0.2 eq) and $Pd_2(dba)_3$ (832 mg, 0.09 mmol, 0.1 eq) were added under nitrogen protection, the reaction solution was heated to 80° C. and stirred for 20 hours, then heated to 100° C. and stirred for 2 hours. After cooling to room temperature, the reaction solution was filtered, the solid was washed with ethyl acetate (200 mL), the combined filtrate was washed with water and saturated sodium chloride solution, then dried over anhydrous sodium sulfate, and concentrated to obtain crude compound 10 (6.0 g), which was directly used for the next reaction without purification.

LCMS: $[M+H]^+$=431.1

Step 8. Compound 11

Compound 10 (crude, 6.0 g, 9.09 mmol, 1.0 eq) was dissolved in dichloromethane (200 mL), hydrochloric acid aqueous solution (4M, 100 mL) was added, and stirred at room temperature for 2 hours. The reaction solution was separated, the organic phase was washed with aqueous hydrochloric acid (4M, 3×30 mL), and the pH of the combined aqueous phase was adjusted to be 8 with sodium carbonate to obtain an aqueous solution of compound 11 (about 200 mL).

LCMS: $[M+H]^+$=167.1

Step 9. Compound 12

$Boc_2O$ (4.0 g, 18 mmol, 2.0 eq) in tetrahydrofuran (100 mL) was added to the aqueous solution of Compound 11 (about 200 mL), and the reaction solution was stirred at room temperature for 4 hours. The reaction solution was extracted with ethyl acetate (3×50 mL), the combined organic phase was washed with saturated sodium chloride solution, dried over anhydrous sodium sulfate, and the residue obtained after concentration was purified by silica gel column chromatography (petroleum ether/ethyl acetate=5/1) to obtain compound 12 (3.0 g, yield of three-step: 90%).

LCMS: $[M+Na]^+$=389.1

Step 10. Compound 13

Compound 12 (2.8 g, 7.65 mmol, 1.0 eq) was dissolved in a solution of hydrogen chloride in methanol (4M, 40 mL), and the mixture was stirred at room temperature for 2 hours. The reaction solution was concentrated to obtain compound 13 (2.0 g) as a white solid.

LCMS: $[M+H]^+$=167.1

Step 11. Compound 14

Compound 13 (2.0 g) was dissolved in tetrahydrofuran (50 mL), the pH value was adjusted to be 8 with sodium carbonate aqueous solution, and $Boc_2O$ (1.5 g, 6.88 mmol, 0.9 eq) was added. The reaction solution was stirred at room temperature for 10 minutes and then extracted with ethyl acetate (3×60 mL), the combined organic phase was washed with saturated sodium chloride solution, dried over anhydrous sodium sulfate, and the residue obtained after concentration was purified by silica gel column chromatography (petroleum ether:ethyl acetate=3:1) to obtain compound 14 (0.85 g, yield of two-step: 42%).

LCMS: $[M+H]^+$=267.1

Step 12. Compound 15

Compound 14 (0.8 g, 3.0 mmol, 1.0 eq) was dissolved in a mixed solvent of dichloromethane (100 mL) and methanol (10 mL), calcium carbonate (2.1 g, 21.03 mmol, 7.0 eq) was added, the temperature was cooled to 0° C. under nitrogen protection, and $BnMe_3NBr_3$ (4.5 g, 11.5 mmol, 4.0 eq) was slowly added to the reaction solution in batches, the reaction solution was heated to room temperature and stirred for half an hour. The reaction solution was filtered and the solid was washed with dichloromethane (100 mL). The combined filtrate was washed with a mixed aqueous solution of sodium bicarbonate and sodium sulfite, the organic phase was dried over anhydrous sodium sulfate and concentrated, and the residue was purified by silica gel column chromatography (petroleum ether/ethyl acetate=5/1) to obtain compound 15 (1.1 g, yield 80%) as a white solid.

LCMS: $[M+Na]^+$=446.8

Step 13, Compound 17

Compound 17 (1.0 g, 2.36 mmol, 1.0 eq) was dissolved in 1,4-dioxane (100 mL), methyl boric acid (1.13 g, 18.86 mmol, 4.0 eq), potassium phosphate (2.5 g, 11.79 mmol, 5.0 eq) and $Pd(dppf)Cl_2$ (289 mg, 0.35 mmol, 0.15 eq) were added, the temperature was heated to 120° C. under the condition of nitrogen protection, and the reaction solution was stirred for 8 hours. The reaction solution was cooled to room temperature and then filtered. After the filtrate was concentrated, it was dissolved in water and ethyl acetate and separated. The aqueous phase was extracted with ethyl acetate. The combined organic phase was washed with saturated sodium chloride solution, dried over anhydrous sodium sulfate, and the residue obtained after concentration was purified by silica gel column chromatography (petroleum ether/ethyl acetate=6/1) to obtain compound 17 (650 mg, yield 85%) as a white solid.

LCMS: $[M+H]^+$=295.1

Step 14. Compound 19

Compound 17 (600 mg, 2.04 mmol, 1.0 eq) was dissolved in dichloromethane (20 mL), cooled to 0° C., and triethylamine (515 mg, 5.10 mmol, 2.5 eq) and compound 18 (411 mg, 3.06 mmol, 1.5 eq) were added. The reaction solution was heated to room temperature and stirred for 0.5 h, the reaction solution was diluted with water, and then extracted with dichloromethane (3×50 mL). The combined organic phase was washed with water, dried over anhydrous sodium sulfate, the residue obtained after concentration was slurried with a mixed solvent (petroleum ether/ethyl acetate=40/1) for half an hour, and the solid obtained after filtration was dried to obtain compound 19 (700 mg, yield 87%) as a white solid.

LCMS: $[M+Na]^+$=415.2

Step 15. Compound 20

A solution of Compound 19 (700 mg, 1.78 mmol, 1.0 eq) and hydrogen chloride (4M, 15 mL) in methanol was added to a single-neck flask, and stirred for 0.5 h at room temperature.

After the reaction solution was spin-dried, ethyl acetate was added to dilute, and then the pH value was adjusted to be 8 with sodium carbonate aqueous solution, and the aqueous phase was extracted with ethyl acetate. The combined organic phase was washed with saturated sodium chloride solution, dried over anhydrous sodium sulfate, and concentrated to obtain compound 20 (400 mg, 77%).

LCMS: $[M+H]^+$=293.2

Step 16. Compound H

Compound 20 (180 mg, 0.61 mmol, 1.0 eq), compound 21 (1.08 g, 8.18 mmol, 13.0 eq) and cesium carbonate (2.0 g, 6.1 mmol, 10 eq) were added to N-methylpyrrolidone (10 mL), and the mixture was heated to 180° C. in a microwave reactor under nitrogen and reacted for 4 hours. The reaction solution was cooled to room temperature, diluted with ethyl acetate (150 mL), then washed with saturated sodium chloride solution (80 mL×4), the combined organic phase was dried over anhydrous sodium sulfate, and the residue obtained after concentration was purified by silica gel column chromatography (petroleum ether; ethyl acetate=30/1 to 2/1) to obtain compound H (4.2 mg, yield 17%) as a white solid.

LCMS: $[M+Na]^+$=405.1

$^1$H NMR (400 MHz, DMSO-$d_6$) δ 9.30 (s, 1H), 7.21-7.18 (m, 1H), 7.00-6.96 (m, 1H), 6.82-6.77 (m, 1H), 4.23 (s, 2H), 3.44-3.36 (m, 2H), 2.82-2.73 (m, 2H), 2.24 (s, 2H), 2.04 (s, 3H). 2.01 (s, 3H), 1.07 (s, 9H).

Example 9 Preparation of Compound I

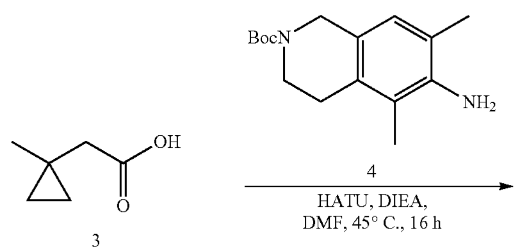

3

4

-continued

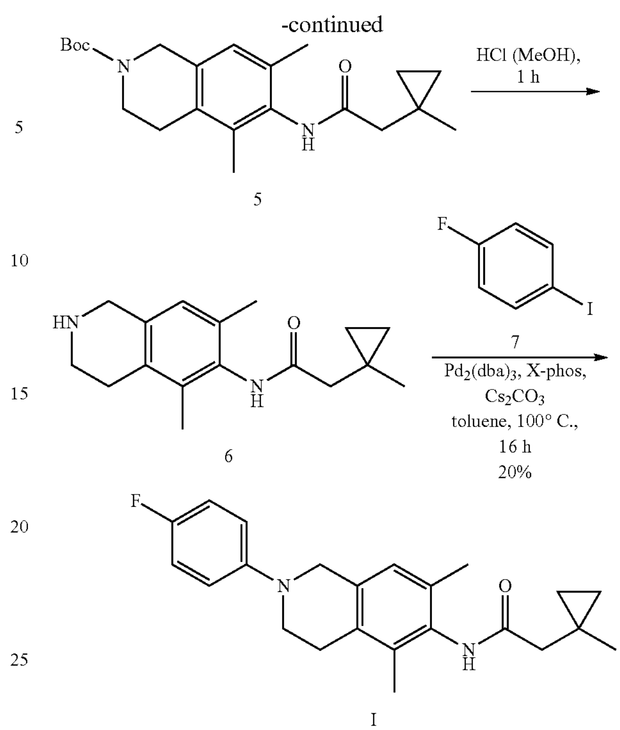

5

6

7

I

Step 1. Compound 5

Compound 3 (1.2 g, 10.8 mmol, 1.5 eq) was dissolved in anhydrous dimethylformamide (5 mL), compound 4 (2.0 g, 7.2 mmol, 1.0 eq), HATU (6.84 g, 18 mmol, 2.5 eq) and diisopropylethylamine (6 mL, 36 mmol, 5.0 eq) were sequentially added, and the reaction solution was heated to 45° C. and stirred for 16 hours. The reaction solution was cooled to room temperature and diluted with water and extracted with ethyl acetate (3×10 mL). The combined organic phase was washed with saturated sodium chloride solution, dried over anhydrous sodium sulfate, and the residue obtained after concentration was purified by silica gel column chromatography (petroleum ether/ethyl acetate=2/1) to obtain compound 5 (2.5 g, yield 62%) as a white solid.

LCMS: $[M+Na]^+$=395.2.

Step 2. Compound 6

Compound 5 (2.5 g, 6.7 mmol, 1.0 eq) and a solution of hydrogen chloride in methanol (4M, 55 mL) were sequentially added to a single-neck flask, and the mixture was stirred at room temperature for 1 hour. The reaction solution was concentrated, and the resulting residue was dissolved in a mixed solvent of dichloromethane/methanol (10/1), then washed with an aqueous sodium carbonate (0.5M, 50 mL), and the aqueous phase was extracted with a mixed solvent of dichloromethane/methanol (10/1,3×20 mL). The combined organic phase was washed with saturated sodium chloride solution, dried over anhydrous sodium sulfate, and concentrated to obtain compound 6 (1.6 g, yield 85%) as a gray solid.

LCMS: $[M+H]^+$=273.2

Step 3. Compound I

Compound 6 (1.4 g, 5.1 mmol, 1.0 eq) was dissolved in toluene (200 mL), and cesium carbonate (3.3 g, 10.2 mmol, 2.0 eq), compound 7 (1.7 g, 7.7 mmol, 1.5 eq), X-Phos (486 mg, 1.02 mmol, 0.2 eq) and $Pd_2(dba)_3$ (467 mg, 0.51 mmol, 0.1 eq) were sequentially added, the temperature was heated to 100° C., and the mixture was stirred for 16 hours under the condition of nitrogen protection. The reaction solution was cooled to room temperature and then filtered, the filtrate was diluted with water and extracted with ethyl acetate (3×20 mL), the combined organic phase was washed with saturated sodium chloride solution, dried over anhydrous sodium sulfate, and the residue obtained after concentration was purified by neutral alumina column chromatography (petroleum ether/ethyl acetate=5/1) to obtain compound I, the crude compound I was further purified by Pre-HPLC (0.1% formic acid/acetonitrile/water) to obtain compound 1 (377.0 mg, 20%) as a white solid.

LCMS: $[M+H]^+$=367.2

$^1H$ NMR (400 MHz, DMSO-$d_6$) δ 9.02 (s, 1H), 7.06-7.03 (m, 4H), 6.91 (s, 1H), 4.26 (s, 2H), 3.50 (s, 2H), 2.74-2.72 (m, 2H), 2.21 (s, 2H), 2.11 (s, 3H), 2.01 (s, 3H), 1.15 (s, 3H), 0.56-0.53 (m, 2H), 0.33-0.31 (m, 2H).

Example 10 Preparation of Compound J

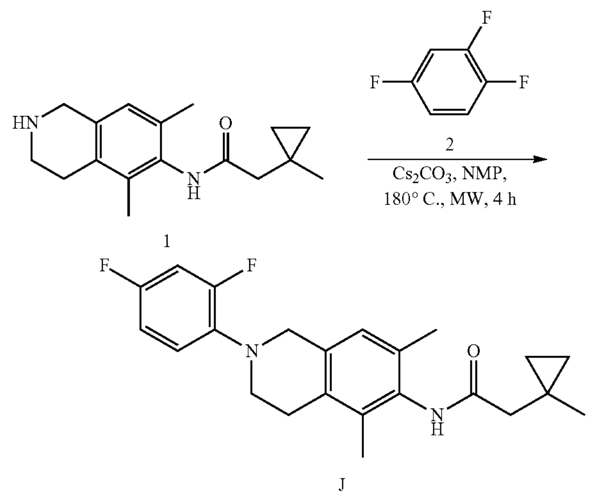

1

J

Step 1. Compound J

Compound 1 (600 mg, 2.20 mmol, 1.0 eq), compound 2 (3.6 g, 27.3 mmol, 12.4 eq) and cesium carbonate (7.19 g, 22.0 mmol, 10 eq) were added to N-methylpyrrolidone (60 mL), and the reaction mixture was heated to 180° C. in a microwave reactor and stirred for 4 hours. After cooling to room temperature, the reaction solution was diluted with ethyl acetate (100 mL), then washed with saturated sodium chloride solution (80 mL×2), dried over anhydrous sodium sulfate, and the residue obtained after concentration was purified by silica gel column chromatography (petroleum ether/ethyl acetate=10/1) to obtain compound J (56.0 mg, 0.146 mmol, yield 7%) as a white solid.

LCMS: $[M+H]^+$=385.1

$^1H$ NMR (400 MHz, DMSO-$d_6$) δ 9.01 (s, 1H), 7.19-7.12 (m, 1H), 6.92-6.82 (m, 2H), 6.75-6.67 (m, 1H), 4.16 (s, 2H), 3.37 (t, J=5.6 Hz, 2H), 2.71 (t, J=5.6 Hz, 2H), 2.18 (s, 2H), 2.07 (s, 3H), 1.97 (s, 3H), 1.11 (s, 3H), 0.52-0.50 (m, 2H), 0.29-0.27 (m, 2H).

Example 11 Preparation of Compound K

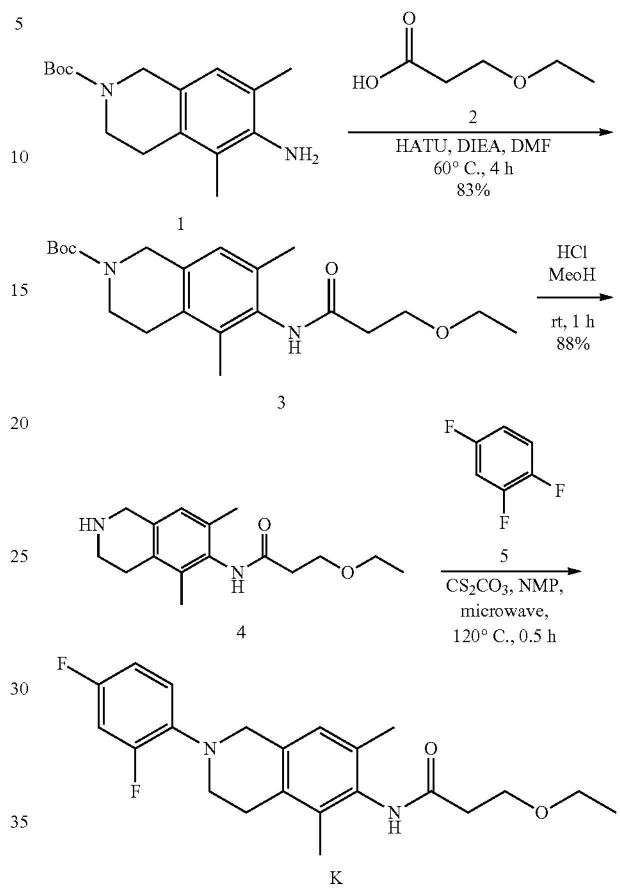

1

3

4

K

Step 1. Compound 3

Compound 1 (200 mg, 0.724 mmol, 1.0 eq) was dissolved in dimethylformamide (5 ml), compound 2 (128 mg, 1.086 mmol, 1.5 eq), HATU (412 mg, 1.086 mmol, 1.5 eq) and diisopropylethylamine (280 mg, 2.172 mmol, 3.0 eq) were added, and the mixture was heated to 60° C. and stirred for 4 hours. The reaction solution was cooled to room temperature and diluted with water (20 mL), and the aqueous phase was extracted with ethyl acetate (3×20 mL). The combined organic phase was washed with saturated sodium chloride solution, dried over anhydrous sodium sulfate, and the residue obtained after concentration was purified by silica gel column chromatography (petroleum ether/ethyl acetate=1/1) to obtain compound 3 (220 mg, yield 83%) as a yellow solid.

LCMS: $[M+H]^+$=377.2

Step 2. Compound 4

Compound 3 (280 mg, 0.745 mmol, 1.0 eq) was dissolved in a solution of hydrogen chloride in methanol (4 M, 10 mL), and the mixture was stirred for 1 hour at room temperature. After concentration, saturated sodium carbonate aqueous solution was added to the residue to adjust the pH value to be 8-9, extracted with ethyl acetate (3×30 mL), the combined organic phase was washed with saturated sodium chloride solution, dried over anhydrous sodium sulfate, and concentrated to obtain compound 4 (180 mg, yield 88%) as a yellow solid.

LCMS: $[M+H]^+=277.2$

Step 3. Compound K

Compound 4 (10 mg, 0.036 mmol, 1.0 eq) was dissolved in N-methylpyrrolidone (1 mL), cesium carbonate (117 mg, 0.36 mmol, 10.0 eq) and compound 5 (58 mg, 0.446 mmol, 12.4 eq) were added, the temperature was heated to 120° C. in a microwave reactor, reacted for 0.5 h, the reaction solution was cooled to room temperature and then concentrated, the residue was purified by prep-HPLC to obtain compound K.

LCMS: $[M+H]^+=389.1$

Example 12 Preparation of Compound L

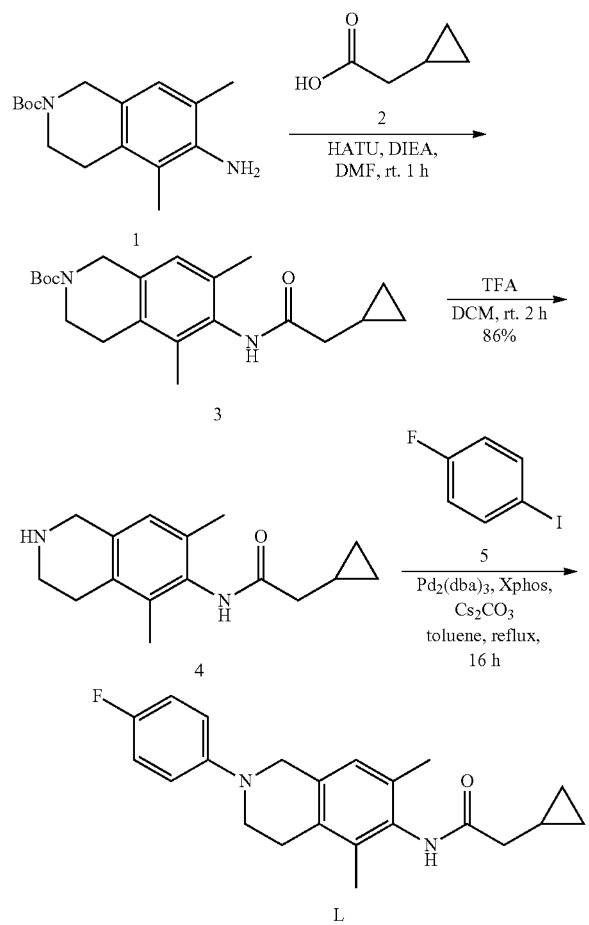

Step 1. Compound 3

Compound 1 (100 mg, 0.54 mmol. 1.0 eq) was dissolved in dimethylformamide (3 mL and compound 2 (81 mg, 0.81 mmol, 1.5 eq), HATU (314 mg, 0.81 mmol, 1.5 eq) and diisopropylethylamine (209 mg, 1.62 mmol, 3.0 eq) were sequentially added, the mixture was reacted at room temperature for 1 hour. The reaction solution was extracted with ethyl acetate (50 mL×3) and saturated sodium chloride solution, the combined organic phase was dried over anhydrous sodium sulfate, and the residue obtained after concentration was purified by silica gel column chromatography (petroleum ether/ethyl acetate=3/2) to obtain compound 3 (130 mg, yield 67%) as a white solid.

LCMS: $[M+Na]^+=381.1$.

Step 2. Compound 4

Compound 3 (130 mg, 0.36 mmol, 1.0 eq) was dissolved in dichloromethane (10 mL), trifluoroacetic acid (2 mL) was added, and the mixture was stirred at room temperature for 2 hours. The reaction solution was concentrated, extracted with ethyl acetate and saturated sodium bicarbonate aqueous solution, the organic phase was dried over anhydrous sodium sulfate, and concentrated to obtain compound 4 (80 mg, yield 86%) as a light yellow oil.

LCMS: $[M+H]^+=259.1$

Step 3. Compound L

Compound 4 (80 mg, 0.31 mmol, 1.0 eq) and compound 5 (103 mg, 0.47 mmol, 1.5 eq) were dissolved in toluene (10 mL), and $Pd_2(dba)_3$ (57 mg, 0.062 mmol, 0.2 eq), x-Phos (30 mg, 0.062 mmol, 0.2 eq) and cesium carbonate (253 mg, 0.78 mmol, 2.5 eq) were added, the reaction solution was heated to 100° C. under the condition of nitrogen protection and reacted for 18 hours. The reaction solution was cooled to room temperature and then concentrated.

The obtained residue was purified by silica gel column chromatography (petroleum ether/ethyl acetate=1/1) to obtain compound L (8.8 mg, yield 8%) as a white solid.

LCMS: $[M+H]^+=353.1$ $^1H$ NMR (400 MHz, $CDCl_3$) δ 7.23 (s, 1H), 7.02-6.93 (m, 4H), 6.90 (s, 1H), 4.27 (s, 2H), 3.50-3.47 (m, 2H), 2.84-2.82 (m, 2H), 2.39 (d, J=7.6 Hz, 2H), 2.23 (s, 3H), 2.13 (s, 3H), 1.19-1.11 (m, 1H), 0.77-0.67 (m, 2H), 0.36-0.33 (m, 2H).

Example 13 Preparation of Compound M

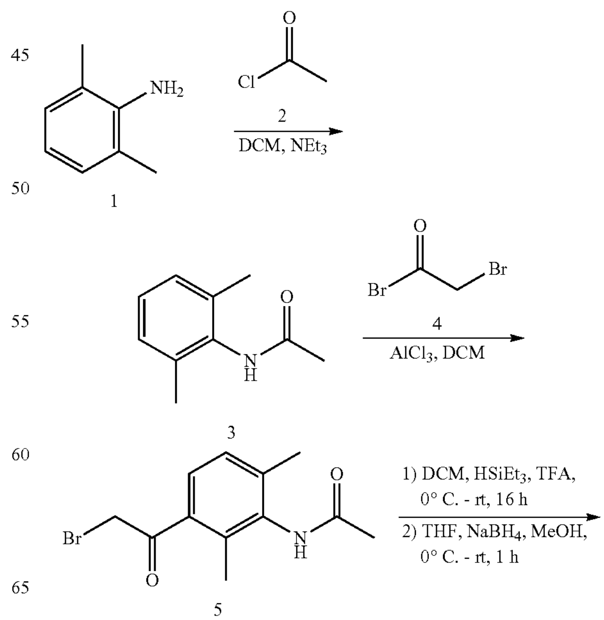

-continued

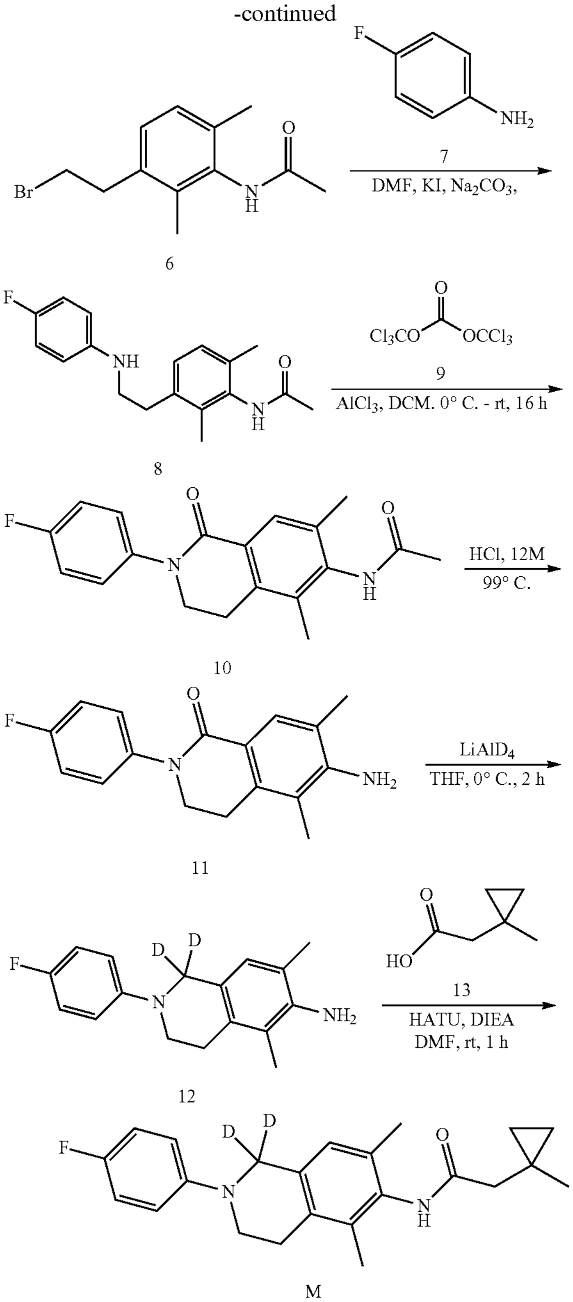

Step 1. Compound 3

Compound 1 (6.0 g, 49.5 mmol, 1.0 eq) and diisopropylethylamine (12.8 g, 99.0 mmol, 2.0 eq) were added to methylene chloride (100 mL), the above solution was cooled to 0° C. under nitrogen protection, and compound 2 (5.83 g, 74.3 mmol, 1.5 eq) was slowly added to the reaction solution, the reaction solution was reacted at room temperature for 2 hours under the condition of nitrogen protection. The reaction solution was concentrated, and the obtained residue was purified by silica gel column chromatography (petroleum ether/ethyl acetate=1:1) to obtain a white solid 3 (6.0 g, yield 74%).

LCMS: $[M+H]^+$=164.1.

Step 2. Compound 5

Aluminum trichloride (9.6 g, 72.0 mmol, 3.0 eq) was added to dichloromethane (100 mL), the reaction mixture was cooled to 0° C. under nitrogen protection, and compound 3 (4.0 g, 24.0 mmol, 1.0 eq) and compound 4 (7.4 g, 36.6 mmol, 1.5 eq) in dichloromethane (50 mL) solution were slowly added. The reaction solution was slowly heated to room temperature and stirred for 16 hours, diluted with dichloromethane (100 mL), and then washed with ice water (5×200 mL). The separated organic phase was dried over anhydrous sodium sulfate and concentrated to obtain crude compound 5 (6.0 g). The crude compound 5 was slurried with a mixed solvent of dichloromethane/petroleum ether (20 mL/40 mL) and filtered to obtain compound 5 (4.0 g, yield 58%) as a white solid.

LCMS: $[M+H]^+$=284.0

Step 3. Compound 6

Compound 5 (2.0 g, 7.0 mmol, 1.0 eq) was dissolved in dichloromethane (10 mL), $HSiEt_3$ (10 mL) was added, the reaction solution was cooled to 0° C. under nitrogen protection, trifluoroacetic acid (10 mL) was slowly added, the reaction solution was slowly heated to room temperature and stirred for 16 hours. The above reaction solution was concentrated, the resulting residue was dissolved with tetrahydrofuran (30 mL), then the temperature was cooled to 0° C. under nitrogen protection, sodium borohydride (532 mg, 14 mmol, 2.0 eq) was slowly added, heated to room temperature, and the mixture was stirred for 0.5 h. The above reaction solution was cooled to 0° C. under the condition of nitrogen protection, methanol (10 mL) was slowly added dropwise, and the residue obtained after concentration of the reaction solution was purified by silica gel column chromatography (petroleum ether:ethyl acetate=2:1) to obtain compound 6 (2.0 g, yield 100%) as a white solid.

LCMS: $[M+H]^+$=270.0.

Step 4. Compound 8

Compound 6 (2.0 g, 7.0 mmol, 1.0 eq), compound 7 (1.65 g, 14.8 mmol, 2.1 eq), potassium iodide (1.23 g, 7.0 mmol, 1.0 eq) and potassium carbonate (2.35 g, 22 mmol, 3.0 eq) were added to dimethylformamide (10 mL) under nitrogen protection, and the reaction solution was heated to 90° C. and stirred for 16 hours. After cooling to room temperature, the reaction solution was diluted with ethyl acetate (200 mL) and filtered, the filtrate was washed with saturated sodium chloride solution, the organic phase was dried over anhydrous sodium sulfate, and the residue obtained after concentration was purified by silica gel column chromatography (petroleum ether:ethyl acetate=2:1) to obtain compound 8 (1.0 g, yield 45%) as a white solid.

LCMS: $[M+H]^+$=301.1

Step 5. Compound 10

Compound 8 (600 mg, 2.0 mmol, 1.0 eq) was dissolved in dichloromethane (20 mL), compound 9 (296 mg, 1.0 mmol, 0.5 eq) was added, and stirred at room temperature for 1 hour under nitrogen protection. The reaction solution was cooled to 0° C., aluminum trichloride (800 mg, 6.0 mmol, 3.0 eq) was added, the temperature was slowly heated to room temperature, and the reaction solution was stirred for 16 hours. The reaction solution was diluted with dichloromethane (100 mL), washed with ice water, the organic phase was dried over anhydrous sodium sulfate, and the residue obtained after concentration was purified by silica gel column chromatography (petroleum ether/ethyl acetate=2/1) to obtain compound 10 (200 mg, yield 30%) as a white solid.

LCMS: $[M+H]^+$=327.1

Step 6. Compound 11

Compound 10 (190 mg, 0.6 mmol) was dissolved in concentrated hydrochloric acid (12M, 15 mL), and the temperature was heated to 99° C., and the reaction was stirred for 64 hours under nitrogen protection. After cooling to room temperature, the reaction solution was concentrated, and the obtained residue was azeotropic with toluene and ethanol to remove water to obtain a crude compound 11 (200 mg) as a white solid.

LCMS: $[M+H]^+$=285.2

Step 7. Compound 12

Compound 11 (200 mg, 0.6 mmol) was dissolved in tetrahydrofuran (50 mL), cooled to 0° C., $LiAlD_4$. (252 mg, 6.0 mmol, 10.0 eq) was slowly added, then the temperature was heated to room temperature, and the mixture was stirred for 16 hours. The reaction solution was diluted with tetrahydrofuran (250 mL) and cooled to 0° C., sodium sulfate decahydrate (10 g) was added, and the reaction solution was stirred for 0.5 h, and the residue obtained after filtration and concentration of the reaction solution was purified by silica gel column chromatography (petroleum ether/ethyl acetate=2/1) to obtain compound 12 (25 mg, yield in two-step: 15%) as a yellow solid.

LCMS: $[M+H]^+$=273.1

Step 8. Compound M

Compound 13 (21 mg, 0.183 mmol, 2.0 eq), HATU (70 mg, 0.183 mmol, 2.0 eq) and diisopropylethylamine (36 mg, 0.275 mmol, 3.0 eq) were dissolved in dimethylformamide (5 mL), and the reaction solution was stirred at room temperature for 0.5 h under nitrogen protection. Compound 12 (25 mg, 0.092 mmol, 1.0 eq) was added to the above reaction solution, and the temperature was heated to 45° C., and the reaction solution was stirred for 16 hours. The reaction solution was diluted with ethyl acetate (50 mL), washed with saturated sodium chloride solution, the organic phase was dried over anhydrous sodium sulfate, and the residue obtained after concentration was purified by silica gel column chromatography (petroleum ether/ethyl acetate=2/1) to obtain compound M (2.3 mg, yield 6.8%) as a white solid.

LCMS: $[M+H]^+$=369.2

$^1H$ NMR (400 MHz, $CDCl_3$) δ 7.18 (s, 1H), 7.01-6.86 (m, 5H), 3.47 (t, J=5.6 Hz, 2H), 2.81 (t, J=5.6 Hz, 2H), 2.38 (s, 2H), 2.22 (s, 3H), 2.12 (s, 3H), 1.28 (s, 3H), 0.60-0.50 (m, 4H).

Example 14 Preparation of Compound N

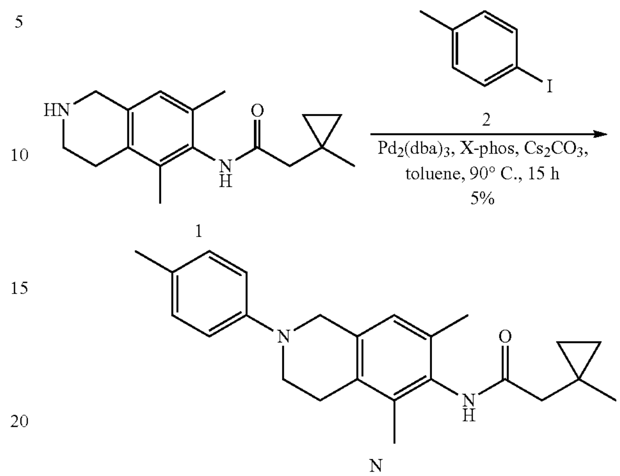

1

N

Step 1. Compound N

Compound 1 (30 mg, 0.11 mmol, 1.0 eq) was dissolved in toluene (13 mL), and cesium carbonate (384 mg, 0.33 mmol, 3.0 eq), compound 2 (37 mg, 0.17 mmol, 1.5 eq), x-Phos (11 mg, 0.02 mmol, 0.2 eq) and $Pd_2(dba)_3$ (11 mg, 0.01 mmol, 0.1 eq) were sequentially added, the temperature was heated to 90° C., and the mixture was stirred for 15 hours under the condition of nitrogen protection. The reaction solution was cooled to room temperature, diluted with water, extracted with ethyl acetate (3×20 mL), the organic phase was combined and washed with saturated sodium chloride solution, dried over anhydrous sodium sulfate, and the residue obtained after concentration was purified by Pre-HPLC (0.1% formic acid/acetonitrile/water) to obtain compound N (2 mg, yield 5%) as a white solid.

LCMS: $[M+H]^+$=363.2

$^1H$ NMR (400 MHz, DMSO-$d_6$) δ 9.02 (s, 1H), 7.04-7.02 (m, 2H), 6.93-6.91 (m, 3H), 4.25 (s, 2H), 3.49 (s, 2H), 2.51-2.49 (m, 2H), 2.21 (s, 2H), 2.20 (s, 3H), 2.11 (s, 3H), 2.01 (s, 3H), 1.15 (s, 3H), 0.56-0.53 (m, 2H), 0.33-0.31 (m, 2H).

Example 15 Preparation of Compound O

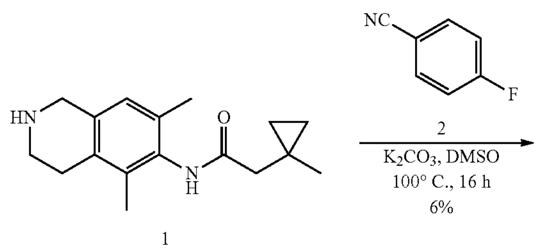

1

-continued

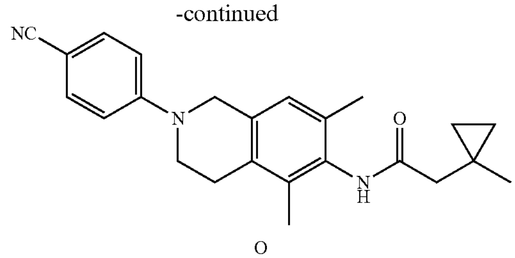

O

Step 1. Compound O

Compound 1 (50 mg, 0.183 mmol, 1.0 eq) was dissolved in dimethyl sulfoxide (5 mL), compound 2 (33 mg, 0.275 mmol, 1.5 eq) and potassium carbonate (76 mg, 0.275 mmol, 1.5 eq) were added, and the temperature was heated to 100° C., and the mixture was stirred for 16 hours. After cooling to room temperature, the mixture was diluted with water, extracted with ethyl acetate (3×20 mL), the combined organic phase was washed with saturated sodium chloride solution, dried over anhydrous sodium sulfate, and the residue obtained after concentration was purified by pre-HPLC (0.1% ammonia/acetonitrile/water) to obtain compound O (4.2 mg, yield 6%) as a white solid.

LCMS: $[M+H]^+$=374.1

$^1$H NMR (400 MHz, DMSO-$d_6$) δ 9.02 (s, 1H), 7.56 (d, J=9.0 Hz, 2H), 7.04 (d, J=9.1 Hz, 2H), 6.92 (s, 1H), 4.47 (s, 2H), 3.66 (s, 2H), 2.74 (t, J=5.7 Hz, 2H), 2.18 (s, 2H), 2.09 (s, 3H), 2.00 (s, 3H), 1.12 (s, 3H), 0.51 (q, J=4.2 Hz, 2H), 0.29 (q, J=4.1 Hz, 2H).

Example 16 Preparation of Compound P

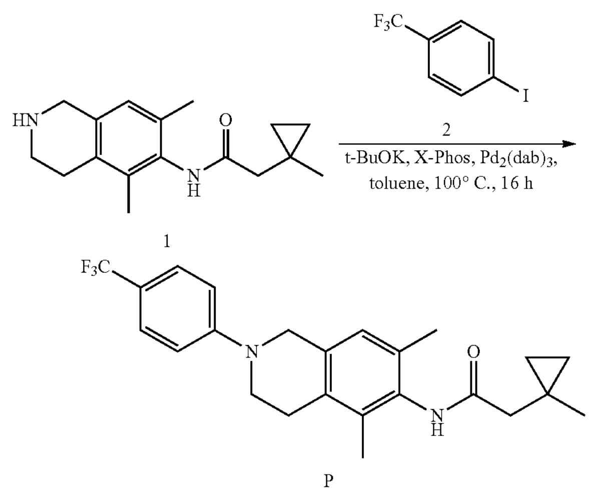

1

P

Step 1. Compound P

Compound 1 (30 mg, 0.110 mmol, 1.0 eq) was dissolved in toluene (5 mL), compound 2 (45 mg, 0.165 mmol, 1.5 eq), potassium tert-butoxide (37 mg, 0.330 mmol, 3.0 eq), X-Phos (11 mg, 0.022 mmol, 0.2 eq) and $Pd_2(dba)_3$ (10 mg, 0.011 mmol, 0.1 eq) were added, the temperature was heated to 100° C., and the mixture was stirred for 16 hours under the condition of nitrogen protection. After cooling to room temperature, the reaction solution was diluted with ethyl acetate (30 mL), then washed with water and saturated sodium chloride solution in turn, the organic phase was dried over anhydrous sodium sulfate, and the residue obtained after concentration was purified by Pre-HPLC (0.1% formic acid/acetonitrile/water) to obtain compound P (6.3 mg, yield 13%) as a white solid.

LCMS: $[M+H]^+$=417.1

$^1$H NMR (400 MHz, DMSO-$d_6$) δ 9.05 (s, 1H), 7.51 (d, J=8.7 Hz, 2H), 7.12 (d, J=8.7 Hz, 2H), 6.96 (s, 1H), 4.46 (s, 2H), 3.68 (s, 2H), 2.77 (s, 2H), 2.22 (s, 2H), 2.12 (s, 3H), 2.03 (s, 3H), 1.15 (s, 3H), 0.55 (s, 2H), 0.33-0.31 (m, 2H).

Example 17 Preparation of Compound Q

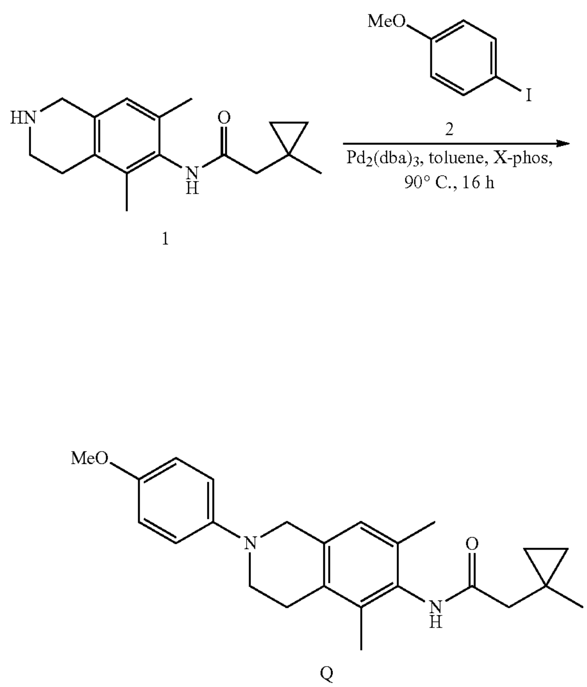

1

Q

Step 1. Compound Q

Compound 1 (40 mg, 0.15 mmol, 1.0 eq) and compound 2 (51.6 mg, 0.22 mmol, 1.5 eq) were dissolved in toluene (5 mL), and $Pd_2(dba)_3$ (14 mg, 0.015 mmol, 0.1 eq), Xant-Phos (14 mg, 0.03 mmol, 0.2 eq) and cesium carbonate (143 mg, 0.45 mmol, 3.0 eq) were added, the temperature was heated to 90° C., and the mixture was reacted for 16 hours under the condition of nitrogen protection. After cooling to room temperature, the reaction solution was concentrated, and the resulting residue was purified by Pre-HPLC (0.1% formic acid/acetonitrile/water) to obtain compound Q (9.7 mg, yield 18%) as a white solid.

LCMS: $[M+H]^+$=379.2

$^1$H NMR (400 MHz, $CDCl_3$) δ 7.18 (s, 1H), 6.98 (d, J=8.8 Hz, 2H), 6.92-6.83 (m, 3H), 4.23 (s, 2H), 3.78 (s, 3H), 3.44 (t, J=5.6 Hz, 2H), 2.83 (t, J=5.6 Hz, 2H), 2.40 (s, 2H), 2.23 (s, 3H), 2.13 (s, 3H), 1.30 (s, 3H), 0.61-0.54 (m. 4H).

Example 18 Preparation of Compound R

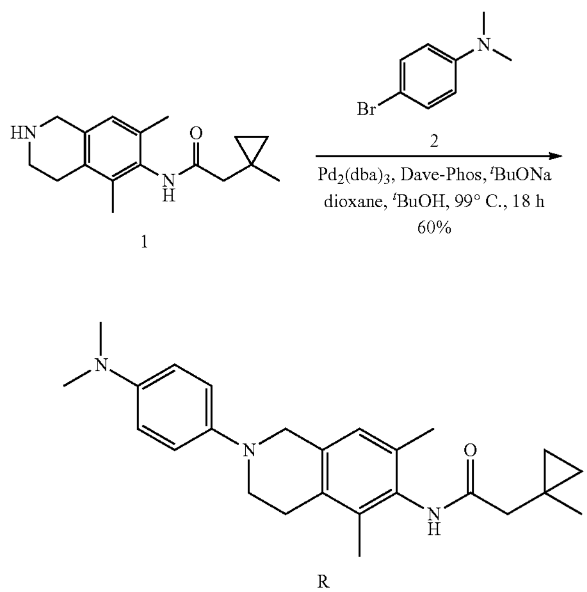

1

R

Step 1. Compound R

Compound 1 (30 mg, 0.11 mmol, 1.0 eq), compound 2 (33 mg, 0.17 mmol, 1.5 eq), sodium tert-butoxide (32 mg, 0.33 mmol, 3.0 eq), Dave-Phos (17 mg, 0.044 mmol, 0.4 eq) and $Pd_2(dba)_3$ (20 mg, 0.022 mmol, 0.2 eq) were dissolved in 1, 4-dioxane (4 mL) and tert-butanol (2 mL), the temperature was heated to 99° C., and the mixture was reacted for 18 hours under nitrogen protection. After cooling, to room temperature, the reaction solution was extracted with ethyl acetate and saturated sodium chloride solution, the organic phase was dried over anhydrous sodium sulfate, and the residue obtained after concentration was purified by silica gel column chromatography (petroleum ether/ethyl acetate=3/1) to obtain compound R (26 mg, yield 60%) as a yellow solid.

LCMS: $[M+H]^+$=392.2

$^1$H NMR (400 MHz, MeOD) δ 7.15 (s, 1H), 7.01 (d, J=7.6 Hz, 2H), 6.93 (d, J=8.0 Hz, 2H), 4.50 (s, 2H), 2.93-2.90 (m, 2H), 2.85-2.83 (m, 2H), 2.81 (s, 3H), 2.80 (s, 3H), 2.23 (s, 2H), 2.11 (s, 3H), 2.02 (s, 3H), 1.12 (s, 3H), 0.53-0.50 (m, 2H), 0.33-0.31 (m, 2H).

Example 19 Preparation of Compound S

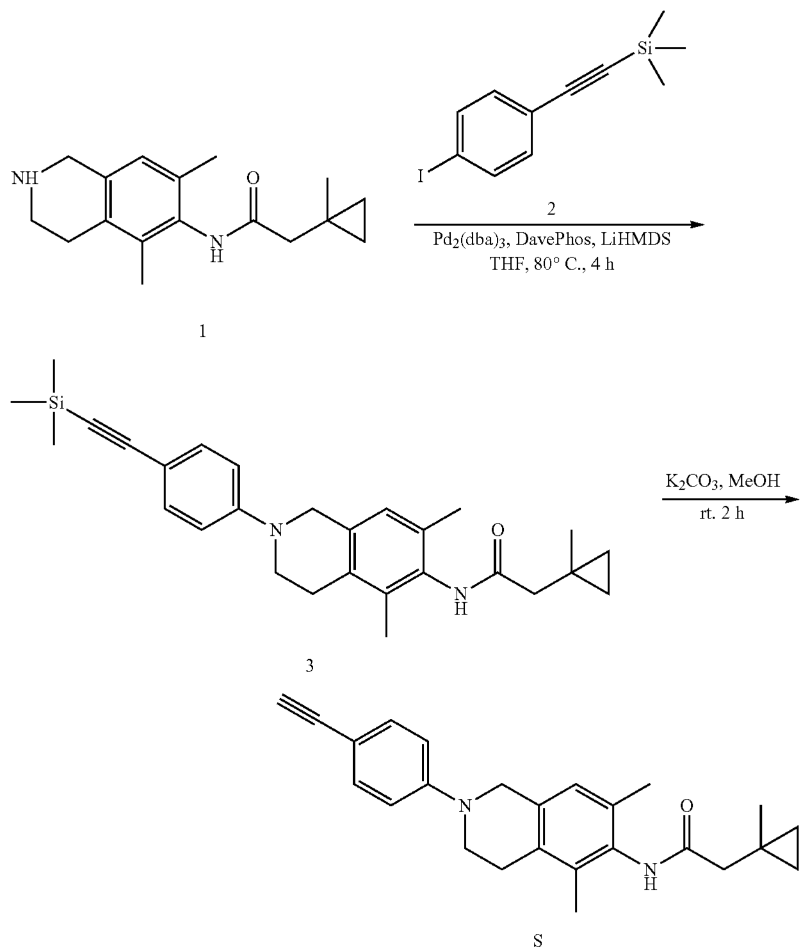

1

3

S

Step 1. Compound 3

Compound 1 (50 mg, 0.18 mmol, 1.0 eq) was dissolved in tetrahydrofuran (15 mL), and compound 2 (83 mg, 0.26 mmol, 1.5 eq), $Pd_2(dba)_3$ (17 mg, 0.018 mmol, 0.1 eq), Dave-Phos (14 mg, 0.036 mmol, 0.2 eq) and LiHMDS (1 M, 1.8 mL, 1.8 mmol, 10 eq) were added, the temperature was heated to 80° C., and the mixture was stirred for 4 hours under the condition of nitrogen protection. The reaction solution was cooled to room temperature and then extracted with ethyl acetate and saturated sodium chloride solution, the organic phase was dried over anhydrous sodium sulfate, and the residue obtained after concentration was purified by silica gel column chromatography (petroleum ether/ethyl acetate=5/1) to obtain compound 3 (4 mg, yield 5%) as a yellow solid.

LCMS: $[M+H]^+$=445.2

Step 2. Compound S

Compound 3 (4 mg, 0.009 mmol, 1.0 eq) and potassium carbonate (4 mg, 0.027 mmol, 3.0 eq) were added to methanol (5 mL), and the mixture was stirred at room temperature for 2 hours. The reaction solution was filtered and the obtained solution was concentrated to obtain compound S (3 mg, yield 90%) as a yellow solid.

LCMS: $[M+H]^+$=373.2

Example 20 Preparation of Compound T

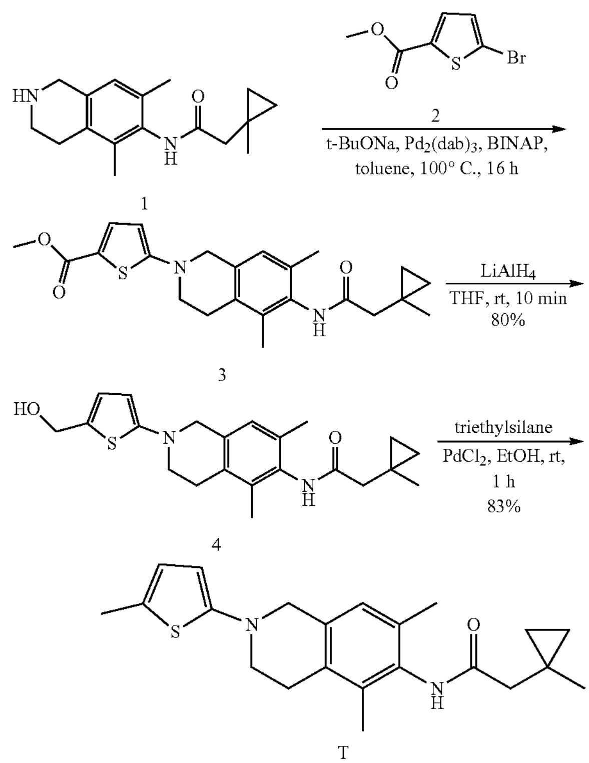

1

3

4

T

Step 1. Compound 3

Compound 1 (80 mg, 0.293 mmol, 1.0 eq) was dissolved in toluene (5 mL), compound 2 (129 mg, 0.587 mmol, 2.0 eq), sodium tert-butoxide (56 mg, 0.587 mmol, 2.0 eq), BINAP (37 mg, 0.0587 mmol, 0.2 eq) and $Pd_2(dba)_3$ (27 mg, 0.0293 mmol, 0.1 eq) were added, the temperature was heated to 100° C., and the mixture was stirred for 16 hours under the condition of nitrogen protection. After cooling to room temperature, the reaction solution was diluted with ethyl acetate (30 mL), then washed with water and saturated sodium chloride solution in turn, the organic phase was dried over anhydrous sodium sulfate, and the residue obtained after concentration was purified by silica gel column chromatography (petroleum ether/ethyl acetate=2/1) to obtain compound 3 (30 mg, yield 25%) as a brown solid.

LCMS: [M+H]+=413.1

Step 2. Compound 4

Compound 3 (20 mg, 0.0484 mmol, 1.0 eq) was dissolved in tetrahydrofuran (3 mL), tetrahydroaluminum lithium (9 mg, 0.2424 mmol, 5.0 eq) was added, the mixture was stirred at room temperature for 10 minutes under nitrogen protection, tetrahydrofuran (5 mL) was added to dilute, and the reaction solution was cooled to 0° C., sodium sulfate decahydrate (0.3 g) was added, and the mixture was stirred at 0° C. for 15 minutes. The reaction solution was filtered and concentrated to obtain compound 4 (15 mg, yield 80%) as a brown solid.

LCMS: [M+H]+=385.1

Step 2. Compound T

Compound 4 (10 mg, 0.026 mmol, 1.0 eq) was dissolved in anhydrous ethanol (1 mL), triethylsilane (3 mg, 0.026 mmol, 1.0 eq) and palladium chloride (2 mg, 0.013 mmol, 0.5 eq) were added, and stirred at room temperature for 1 hour under nitrogen protection. The reaction solution was filtered and concentrated to obtain compound T (8 mg, 83%) as a brown solid.

LCMS: [M+H]+=369.1

Example 21 Preparation of Compound U

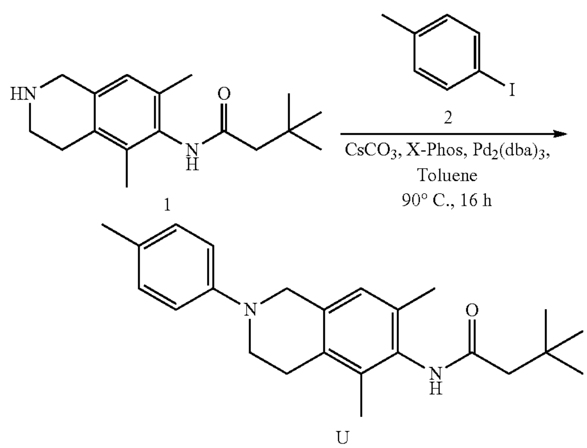

1

U

Step 1. Compound U

Compound 1 (120 mg, 0.4 mmol, 1.0 eq) was dissolved in toluene (40 mL), compound 2 (143 mg, 0.6 mmol, 1.5 eq), cesium carbonate (428.1 mg, 1.31 mmol, 3.0 eq), X-Phos (41.7 mg, 0.08 mmol, 0.2 eq) and $Pd_2(dba)_3$ (40.1 mg, 0.04 mmol, 0.1 eq) were added, the temperature was raised to 90° C. and stirred for 16 hours under the condition of nitrogen protection. After cooling to room temperature, the reaction solution was filtered, the filtrate was diluted with water (30 mL), and extracted with ethyl acetate (3×50 mL). The combined organic phase was washed with saturated sodium chloride solution, dried over anhydrous sodium sulfate, and the residue obtained after concentration was purified by neutral alumina silica gel column chromatography (petroleum ether/ethyl acetate=5/1) to obtain compound U (42.3 mg, yield 26%) as a white solid.

LCMS: $[M+H]^+$=365.2

$^1H$ NMR (400 MHz, DMSO) δ 9.09 (s, 1H), 7.03 (d, J=8.0 Hz, 2H), 6.93-6.90 (m, 3H), 4.24 (s, 2H), 3.50-3.47 (m, 2H), 2.72-2.66 (m, 2H), 2.21 (s, 2H), 2.19 (s, 3H), 2.11 (s, 3H), 2.00 (s, 3H), 1.06 (s, 9H).

Example 22 Preparation of Compound V

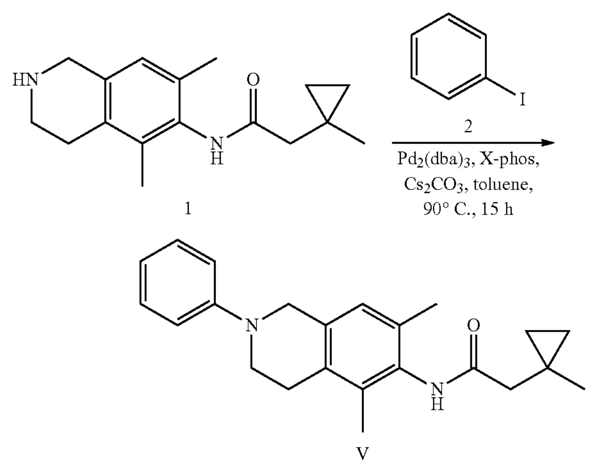

Referring to the synthesis method of compound N, compound V (yield 15%) was obtained.

LCMS: $[M+H]^+$=349.2

$^1H$ NMR (400 MHz, DMSO-$d_6$) δ 9.02 (s, 1H), 7.24-7.20 (m, 2H), 7.02-7.00 (m, 2H), 6.93 (s, 1H), 6.78-6.73 (m, 1H), 4.31 (s, 2H), 3.55 (s, 2H), 2.75-2.72 (m, 2H), 2.21 (s, 2H), 2.12 (s, 3H), 2.02 (s, 3H), 1.15 (s, 3H), 0.56-0.53 (m, 2H), 0.33-0.31 (m, 2H).

Example 23 Preparation of Compound W

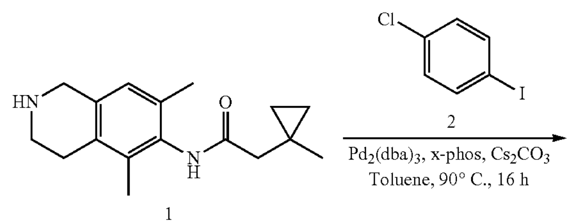

-continued

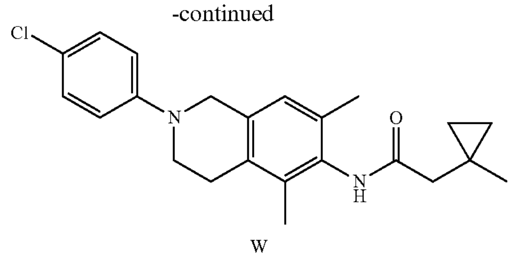

Step 1. Compound W

Compound 1 (50 mg, 0.183 mmol, 1.0 eq) was dissolved in toluene (5 mL) under nitrogen protection, and compound 2 (44 mg, 0.183 mmol, 1.0 eq), $Pd_2(dba)_3$ (17 mg, 0.0183 mmol, 0.1 eq), X-phos (17 mg, 0.0366 mmol, 0.2 eq) and $Cs_2CO_3$ (119 mg, 0.366 mmol, 2.0 eq) were sequentially added, the reaction solution was heated to 90° C. and stirred for 16 hours. After cooling to 25° C., the reaction solution was diluted with ethyl acetate (50 mL), and then washed with water and saturated sodium chloride solution in turn. The organic phase was dried over anhydrous sodium sulfate and concentrated. The obtained residue was purified by pre-HPLC (0.1% formic acid/acetonitrile/water) to obtain compound W (3.2 mg, 5%) as a white solid.

LCMS: $[M+H]^+$=383.1

$^1H$ NMR (400 MHz, DMSO-$d_6$) δ 9.03 (s, 1H), 7.25-7.21 (m, 2H), 7.04-6.99 (m, 2H), 6.92 (s, 1H), 4.32 (s, 2H), 3.55 (s, 2H), 2.73-2.71 (m, 2H), 2.21 (s, 2H), 2.11 (s, 3H), 2.01 (s, 3H), 1.15 (s, 3H), 0.56-0.53 (m, 2H), 0.33-0.31 (m, 2H).

Example 24 Preparation of Compound X

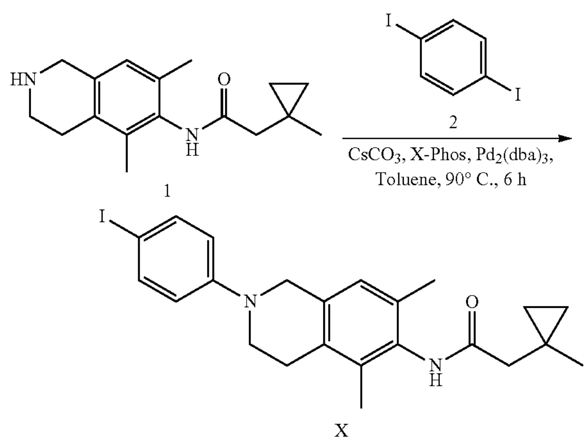

Step 1. Compound X

Compound 1 (300 mg, 1.101 mmol, 1.0 eq) was dissolved in toluene (15 mL), and compound 2 (727 mg, 2.202 mmol, 2.0 eq), cesium carbonate (1.07 g, 3.304 mmol, 3.0 eq), X-PHOS (105 mg, 0.2202 mmol, 0.2 eq) and $Pd_2(dba)_3$ (101 mg, 0.1101 mmol, 0.1 eq) were sequentially added, the reaction solution was heated to 90° C. and stirred for 6 hours under nitrogen protection. After cooling to 25° C., the reaction solution was diluted with ethyl acetate (30 mL), then washed with water and saturated sodium chloride solution in turn, the organic phase was dried over anhydrous sodium sulfate and concentrated, and the residue was purified by silica gel column chromatography (petroleum ether/ethyl acetate=5/1) to obtain compound X (6.3 mg, 1%) as a solid.

LCMS: [M+H]+=475.0

$^1$H NMR (400 MHz, DMSO-$d_6$) δ 9.02 (s, 1H), 7.49-7.46 (m, 2H), 6.92 (s, 1H), 6.86-6.84 (m, 2H), 4.31 (s, 2H), 3.55 (s, 2H), 2.72 (t, J=5.8 Hz, 2H), 2.21 (s, 2H), 2.11 (s, 3H), 2.01 (s, 3H), 1.14 (s, 3H), 0.55-0.53 (m, 2H), 0.33-0.30 (m, 2H).

Example 25 Preparation of Compound Y

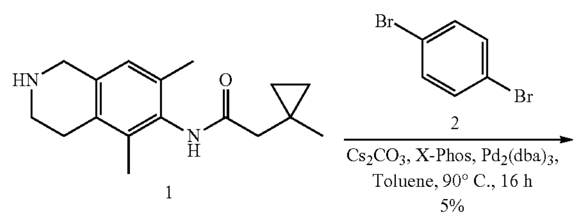

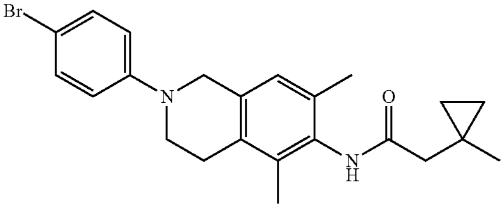

Y

Step 1. Compound Y

Compound 1 (50 mg, 0.183 mmol, 1.0 eq) was dissolved in toluene (5 mL), and compound 2 (87 mg, 0.367 mmol, 2.0 eq), cesium carbonate (179 mg, 0.551 mmol, 3.0 eq), $Pd_2(dba)_3$ (17 mg, 0.018 mmol, 0.1 eq) and X-PHOS (17 mg, 0.036 mmol, 0.2 eq) were added. The reaction solution was heated to 90° C. and stirred for 16 hours, cooled to 25° C., then water (20 mL) was added to dilute, and then extracted with ethyl acetate (3×20 mL). The combined organic phase was washed with saturated sodium chloride solution and dried over anhydrous sodium sulfate. The residue obtained after concentration was purified by pre-HPLC (0.1% formic acid/acetonitrile/water) to obtain compound Y (4.1 mg, 5%) as a white solid.

LCMS: $[M+H]^+$=427.1

$^1$H NMR (400 MHz, $CDCl_3$) δ 7.35-7.33 (m, 2H), 7.18 (s, 1H), 6.91 (s, 1H), 6.84 (d, J=8.9 Hz, 2H). 4.31 (s, 2H), 3.53 (t, J=5.6 Hz, 2H). 2.83 (t, J=5.6 Hz, 2H), 2.39 (s, 2H), 2.24 (s, 3H), 2.14 (s, 3H), 1.29 (s, 3H), 0.61-0.59 (m, 2H), 0.56-0.54 (m, 2H). Example 26

Preparation of Compound Z

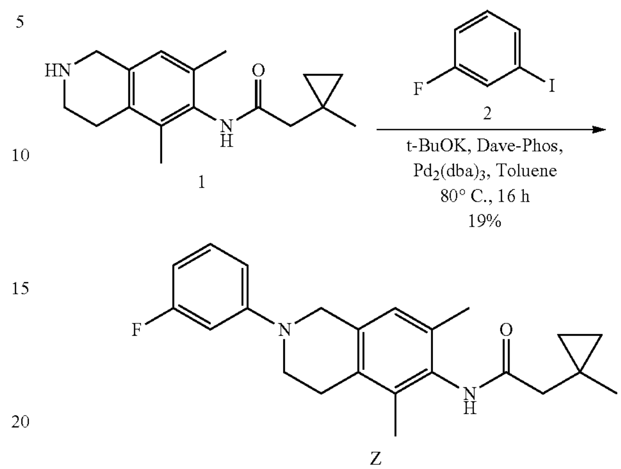

Step 1. Compound Z

Compound 1 (20 mg, 0.074 mmol, 1.0 eq) was dissolved in toluene (5 mL), and compound 2 (24.5 mg, 0.11 mmol, 1.5 eq), potassium tert-butoxide (25 mg, 0.220 mmol, 3.0 eq), Dave-phos (6 mg, 0.015 mmol, 0.2 eq) and $Pd_2(dba)_3$ (7 mg, 0.0074 mmol, 0.1 eq) were sequentially added, the temperature was heated to 80° C., and the mixture was stirred for 16 hours under nitrogen protection. After cooling to 25° C., the reaction solution was diluted with ethyl acetate (30 mL), then washed with water and saturated sodium chloride solution in turn, the organic phase was dried over anhydrous sodium sulfate, and the residue obtained after concentration was purified by silica gel column chromatography (petroleum ether/ethyl acetate=2/1) to obtain compound Z (5.0 mg, 19%) as a white solid.

LCMS: [M+H]+=367.2

$^1$H NMR (400 MHz, $CDCl_3$) δ 7.23-7.17 (m, 2H), 6.93 (s, 1H), 6.72 (d, J=8.4 Hz, 1H), 6.63 (d, J=12.8 Hz, 1H), 6.49 (t, J=8.0 Hz, 1H), 4.35 (s, 2H), 3.56 (t, J=5.6 Hz, 2H), 2.84 (t, J=5.6 Hz, 2H), 2.40 (s, 2H), 2.24 (s, 3H), 2.15 (s, 3H), 1.30 (s, 3H), 0.62-0.54 (m, 4H).

Example 27 Preparation of Compound A12

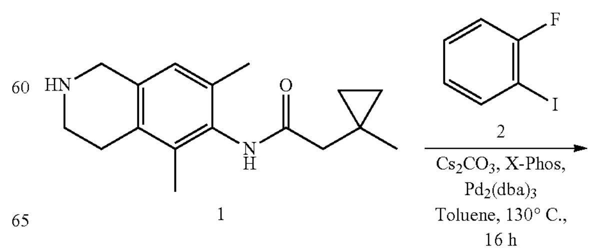

-continued

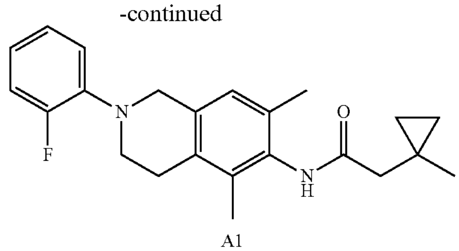

A1

Step 1. Compound A1

Compound 1 (200 mg, 0.734 mmol, 1.0 eq) was dissolved in toluene (50 mL), and compound 2 (1.63 g, 7.34 mmol, 10.0 eq), cesium carbonate (1.2 g, 3.67 mmol, 5.0 eq), X-Phos (140 mg, 0.294 mmol, 0.4 eq) and $Pd_2(dba)_3$ (134 mg, 0.147 mmol, 0.2 eq) were sequentially added. The reaction solution was heated to 130° C. and stirred for 2 hours under nitrogen protection. The reaction solution was cooled to 25° C., diluted with ethyl acetate (20 mL), and then washed with water and saturated sodium chloride solution in turn. The organic phase was dried over anhydrous sodium sulfate and concentrated. The residue was purified by silica gel column chromatography (petroleum ether/ethyl acetate=3/1) to obtain compound A1 (24.3 mg, 9%) as a white solid.

LCMS: $[M+H]^+$=367.2

$^1$H NMR (400 MHz, DMSO-$d_6$) δ 9.04 (s, 1H), 7.19-7.06 (m, 3H), 7.01-6.94 (m, 1H), 6.88 (s, 1H), 4.17 (s, 2H), 3.44-3.35 (m, 2H), 2.79-2.70 (m, 2H), 2.22 (s, 2H), 2.12 (s, 3H), 2.02 (s, 3H), 1.15 (s, 3H), 0.56-0.54 (m, 2H), 0.34-0.31 (m, 2H).

Example 28 Preparation of Compound A2

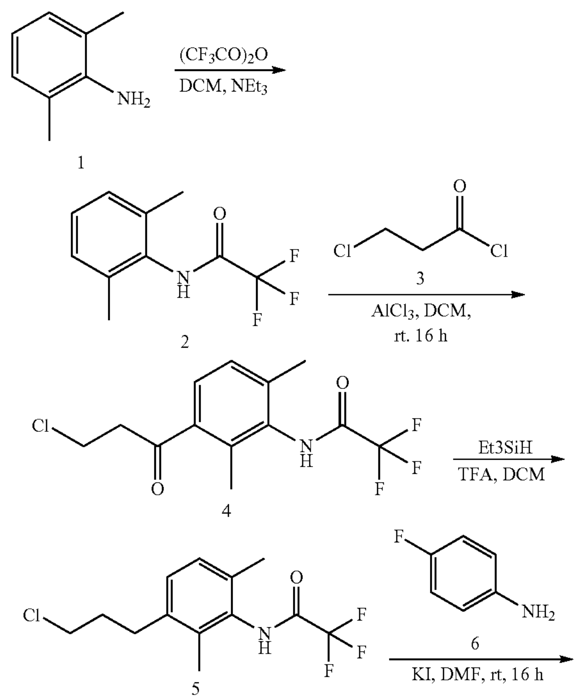

1 2 3 4 5 6

-continued

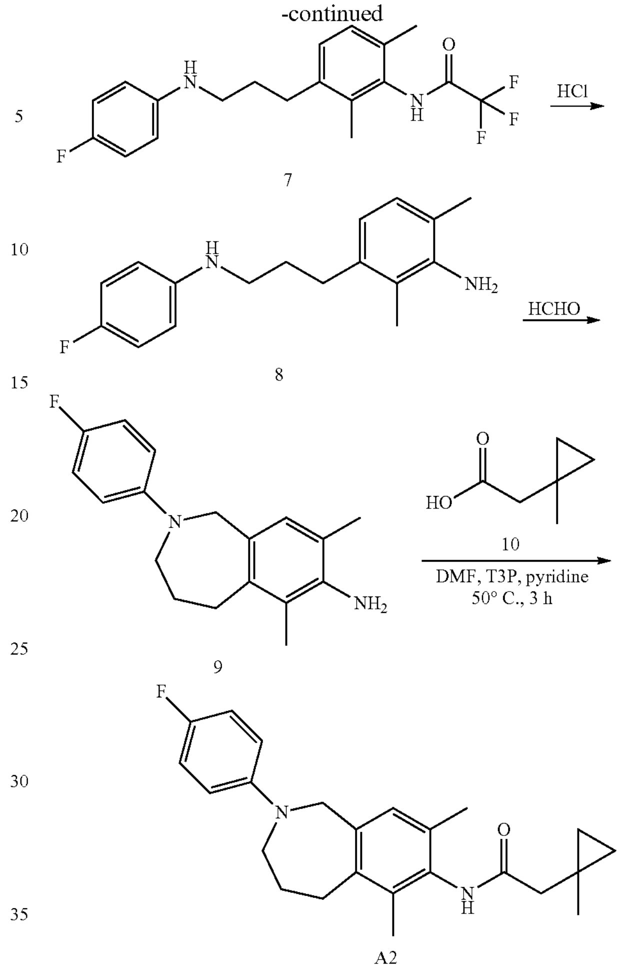

7 8 9 10 A2

Step 1. Compound 2

Compound 1 (10.0 g, 82.5 mmol, 1.0 eq) was dissolved in dichloromethane (100 mL), trifluoroacetic anhydride (26 g, 123.75 mmol, 1.5 eq) was added, the reaction solution was heated to 50° C. and stirred for 1.5 hours. After cooling to 25° C., the reaction solution was concentrated, the residue was dissolved with ethyl acetate (300 mL), and then saturated aqueous sodium bicarbonate was used to adjust the pH value to be 8-9. The separated organic phase was washed with saturated sodium chloride solution and dried over anhydrous sodium sulfate, concentrated to obtain compound 2 (16 g, 89%) as a white solid.

LCMS: $[M+H]^+$=218.1

Step 2. Compound 4

Aluminum trichloride (12.9 g, 96.69 mmol, 3.0 eq) was dissolved in dichloromethane (100 mL), and the mixture was cooled to 0° C., a mixed solution of compound 2 (7.0 g, 32.23 mmol, 1.0 eq) and compound 3 (6.14 g, 48.34 mmol, 1.5 eq) in dichloromethane (20 mL) was added, the reaction solution was heated to 25° C. and stirred for 16 hours under nitrogen protection. Dichloromethane (1 L) was added to dilute the reaction solution, and then the reaction solution was poured into ice water (1.0 L). The organic phase was separated, and the aqueous phase was extracted with ethyl acetate (5×300 mL). The combined organic phase was dried over anhydrous sodium sulfate and concentrated. The residue was purified by silica gel column chromatography (petroleum ether/ethyl acetate=10/1) to obtain compound 4 (3.2 g, 32%) as a white solid.

LCMS: $[M+H]^+$=308.1

Step 3. Compound 5

Compound 4 (3.0 g, 9.75 mmol) was dissolved in trifluoroacetic acid (25 mL), triethylsilane (25 mL) was slowly added dropwise. After the dropwise addition, the reaction solution was heated to 40° C. and stirred overnight. The reaction solution was concentrated, the residue was dissolved with ethyl acetate (300 mL), and then sequentially washed with saturated aqueous sodium bicarbonate and saturated sodium chloride solution, the organic phase was dried over anhydrous sodium sulfate, and the residue obtained after concentration was purified by silica gel column chromatography (petroleum ether/ethyl acetate=10/1) to obtain compound 5 (0.8 g, 28%).

LCMS: $[M+H]^+$=294.1

Step 4. Compound 7

Compound 5 (800 mg, 2.72 mmol, 1.0 eq) was dissolved in N,N-dimethylformamide (10 mL), potassium iodide (452 mg, 2.72 mmol, 1.0 eq) and compound 6 (600 mg, 5.45 mmol, 2.0 eq) were added, the mixture was stirred at 25° C. for 0.5 h, then sodium carbonate (1.15 g, 10.89 mmol, 4.0 eq) was added, and the mixture was continued to be stirred for 16 h. The reaction solution was diluted with ethyl acetate (300 mL), then washed with water and saturated sodium chloride solution in turn. The organic phase was dried with anhydrous sodium sulfate and concentrated. The residue was purified with silica gel column chromatography (petroleum ether/ethyl acetate=10/1) to obtain compound 7 (900 mg, 90%). LCMS: $[M+H]^+$=369.1

Step 5. Compound 8

Compound 7 (800 mg, 1.09 mmol, 1.0 eq) was dissolved in concentrated hydrochloric acid (12 M, 25 mL), and then the mixture was stirred at 99° C. (oil bath temperature) overnight. After cooling the reaction solution to room temperature, the reaction solution was directly used for the next reaction.

LCMS: $[M+H]^+$=273.2

Step 6. Compound 9

Compound 8 of the previous step was added to a formaldehyde aqueous solution (37%, 88 mg, 2.66 mmol, 2.4 eq) at 25° C., and the temperature was heated to 60° C., and the mixture was stirred for 1 hour. The above solution was directly concentrated at 55° C., then a mixed solvent of toluene/ethanol (1:1, 200 mL) was added, and concentrated, and the operation was repeated twice to obtain a crude compound 9 (400 mg) as a yellow solid.

LCMS: $[M+H]^+$=285.2

Step 7. Compound A2

Compound 9 (crude, 200 mg, 0.7 mmol, 1 eq) and compound 10 (241 mg, 2.11 mmol, 3.0 eq) were dissolved in N,N-dimethylformamide (10 mL), pyridine (1.11 g, 14.07 mmol, 20.0 eq) and 1-propyl phosphonic anhydride in ethyl acetate solution (50%, 4.48 g, 7.03 mmol, 10.0 eq) were added under nitrogen protection. The reaction solution was heated to 50° C. under nitrogen protection and stirred for 3 hours. The reaction solution was diluted with ethyl acetate (300 mL), then washed with saturated sodium chloride solution (3×200 mL). The organic phase was dried over anhydrous sodium sulfate and concentrated, and the resulting residue was purified by silica gel column chromatography (petroleum ether/ethyl acetate=4/1 to 2/1) to obtain compound A2 (23.2 mg, yield for three-step: 4.5%) as a white solid.

LCMS: $[M+H]^+$=381.2

$^1$H NMR (400 MHz, DMSO-$d_6$) δ 8.93 (s, 1H), 7.09 (s, 1H), 6.93-6.85 (m, 2H), 6.78-6.74 (m, 2H), 4.53 (s, 2H), 3.75-3.56 (m, 2H), 2.92-2.90 (m, 2H), 2.18 (s, 2H), 2.07 (s, 3H), 2.05 (s, 3H), 1.82-1.66 (m, 2H), 1.13 (s, 3H), 0.59-0.47 (m, 2H), 0.34-0.27 (m, 2H).

Example 29 Preparation of Compound A3

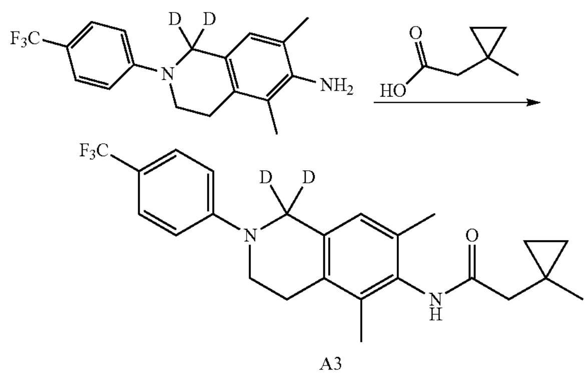

A3

The synthesis method refers to compound M, and compound A3 was obtained as a white solid.

LCMS: $[M+H]^+$=419.3

$^1$H NMR (400 MHz, $CD_3OD$) δ 7.47 (d, J=8.6 Hz, 2H), 7.07 (d, J=8.7 Hz, 2H), 6.99 (s, 1H), 3.70-3.67 (m, 2H), 2.87-2.84 (m, 2H), 2.32 (s, 2H), 2.21 (s, 3H), 2.13 (s, 3H), 1.23 (s, 3H), 0.62-0.60 (m, 2H), 0.43-0.40 (m, 2H).

Example 30 Preparation of Compound A4

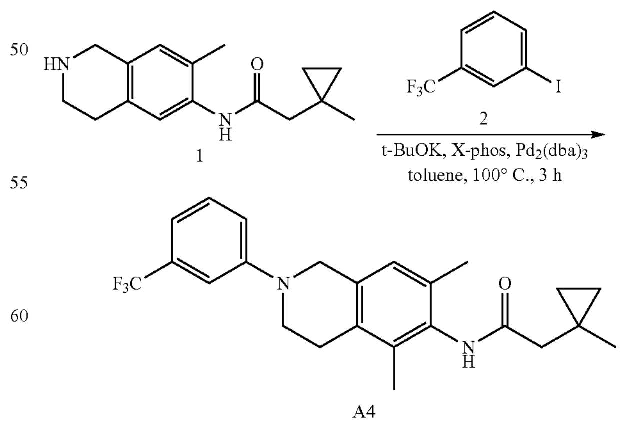

1

A4

Step 1. Compound A4 Compound 1 (150 mg, 0.55 mmol, 1.0 eq) was dissolved in toluene (3 mL), and compound 2

(224 mg, 0.826 mmol, 1.5 eq), potassium tert-butoxide (185 mg, 1.65 mmol, 3.0 eq), X-phos (52 mg, 0.11 mmol, 0.2 eq) and $Pd_2(dba)_3$ (50 mg, 0.05 mmol, 0.1 eq) were sequentially added, and the reaction solution was heated to 100° C. under nitrogen atmosphere and stirred for 3 hours. The reaction solution was cooled to 25° C., diluted with ethyl acetate (50 mL), washed with water and saturated sodium chloride solution in turn. The organic phase was dried over anhydrous sodium sulfate and concentrated, and the residue was purified by pre-HPLC (0.1% formic acid/acetonitrile/water) to obtain compound A4 (36.5 mg, 16%) as a white solid.

LCMS: $[M+H]^+$=417.2

$^1H$ NMR (400 MHz, DMSO-$d_6$) δ 9.03 (s, 1H), 7.42 (t, J=8.0 Hz, 1H), 7.30-7.27 (m, 1H), 7.23 (s, 1H), 7.02 (d, J=7.6 Hz, 1H), 6.97 (s, 1H), 4.41 (s, 2H), 3.63 (s, 2H), 2.77 (t, J=5.7 Hz, 2H), 2.21 (s, 2H), 2.12 (s, 3H), 2.03 (s, 3H), 1.15 (s, 3H), 0.56-0.53 (m, 2H), 0.33-0.31 (m, 2H).

Example 31 Preparation of Compound A5

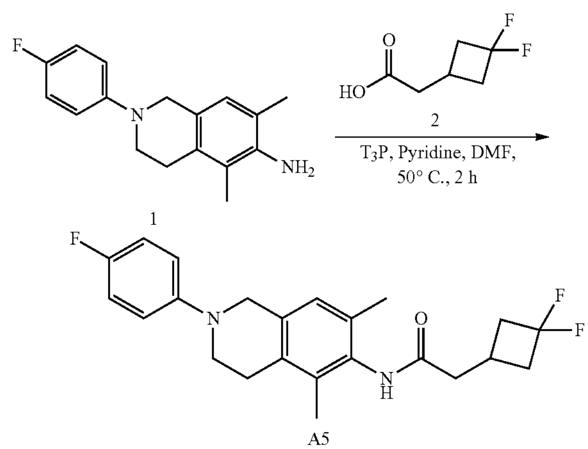

1

A5

Step 1. Compound A5

Compound 1 (100 mg, 0.368 mmol, 1.0 eq) was dissolved in DMF (6 mL), compound 2 (66 mg, 0.44 mmol, 1.2 eq), 1-propyl phosphonic anhydride (50%, 1.17 g, 1.84 mmol, 5.0 eq) and pyridine (582 mg, 7.36 mmol, 20.0 eq) were sequentially added, and the reaction solution was heated to 50° C. under nitrogen atmosphere and stirred for 2 hours. The reaction solution was cooled to 25° C., then diluted with ethyl acetate (50 mL). The resulting solution was washed with water and saturated sodium chloride solution in turn. The organic phase was dried over anhydrous sodium sulfate and then concentrated, and the resulting residue was purified by pre-HPLC (0.1% formic acid/acetonitrile/water) to obtain compound A5 (84.2 mg, 58%) as a white solid.

LCMS: $[M+H]^+$=403.1

$^1H$ NMR (400 MHz, DMSO-$d_6$) δ 9.25 (s, 1H), 7.08-7.00 (m, 4H), 6.91 (s, 1H), 4.26 (s, 2H), 3.49 (s, 2H), 2.77-2.72 (m, 4H), 2.68-2.67 (m, 1H), 2.46-2.44 (m, 1H), 2.40-2.36 (m, 2H), 2.33-2.30 (m, 1H), 2.08 (s, 3H), 1.98 (s, 3H).

Example 32 Preparation of Compound A6

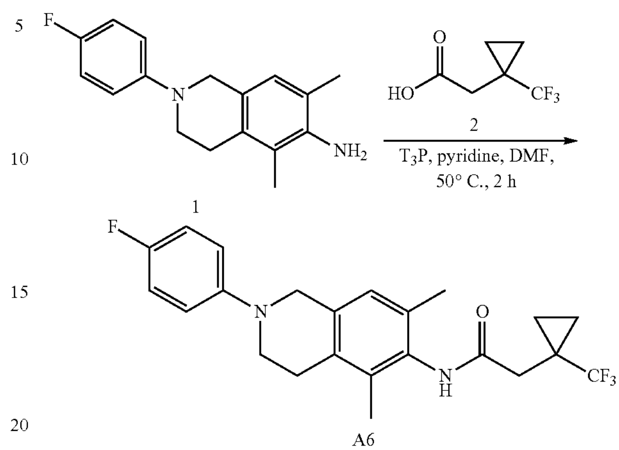

1

A6

Step 1. Compound A6

Compound 1 (50 mg, 0.185 mmol, 1.0 eq) was dissolved in DMF (3 mL), compound 2 (37 mg, 0.222 mmol, 1.2 eq), 1-propyl phosphonic anhydride (50%, 2.4 g, 3.700 mmol, 20.0 eq) and pyridine (146 mg, 1.850 mmol, 10.0 eq) were sequentially added, and the reaction solution was heated to 50° C. and stirred for 2 hours. After cooling to 25° C., the reaction solution was diluted with water (10 mL), and then extracted with ethyl acetate (20×3). The combined organic phase was washed with saturated sodium chloride solution, dried over anhydrous sodium sulfate, and the residue obtained after concentration was purified by pre-HPLC (0.1% formic acid/acetonitrile/water) to obtain compound A6 (8.9 mg, 11%) as a white solid.

LCMS: $[M+H]^+$=421.2

$^1H$ NMR (400 MHz, DMSO-$d_6$) δ 9.31 (s, 1H), 7.08-7.00 (m, 4H), 6.91 (s, 1H), 4.26 (s, 2H), 3.49 (s, 2H), 2.72 (t, J=5.7 Hz, 2H), 2.67 (s, 2H), 2.08 (s, 3H), 1.99 (s, 3H), 1.01 (s, 2H), 0.98 (s, 2H).

Example 33 Preparation of Compound A7

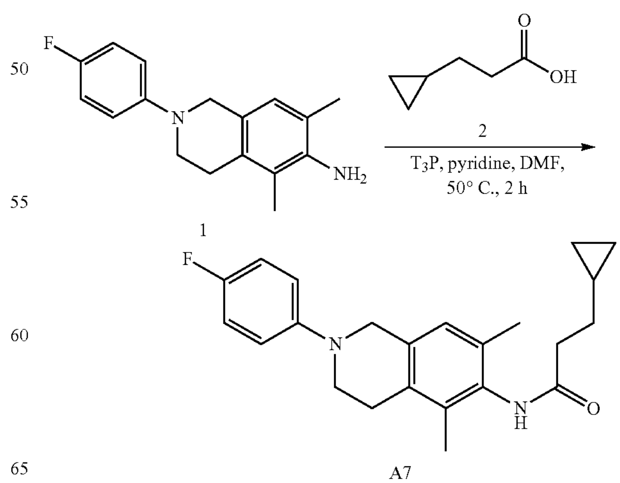

1

A7

Step 1. Compound A7

Compound 1 (50 mg, 0.18 mmol, 1.0 eq) was dissolved in DMF (2 mL), compound 2 (21 mg, 0.18 mmol, 1.0 eq), 1-propyl phosphonic anhydride (50%, 1.15 g, 1.8 mmol, 10.0 eq) and pyridine (284 mg, 1.8 mmol, 10.0 eq) were sequentially added, the temperature was heated to 50° C. and stirred for 2 hours. After cooling to 25° C., the reaction solution was diluted with water (10 mL), and then extracted with ethyl acetate (3×20 mL). The combined organic phase was washed with saturated sodium chloride solution, dried over anhydrous sodium sulfate, and the residue obtained after concentration was purified by pre-HPLC (0.1% formic acid/acetonitrile/water) to obtain compound A7 (4.9 mg, 7%) as a white solid.

LCMS: $[M+H]^+$=367.1

$^1H$ NMR (400 MHz, DMSO-$d_6$) δ 9.18 (s, 1H), 7.09-6.98 (m, 4H), 6.90 (s, 1H), 4.25 (s, 2H), 3.49 (s, 2H), 2.72 (t, J=5, 6 Hz, 2H), 2.39 (t, J=7.6 Hz, 2H), 2.09 (s, 3H), 1.99 (s, 3H), 1.54-1.48 (m, 2H), 0.78-0.71 (m, 1H), 0.45-0.37 (m, 2H), 0.11-0.04 (m, 2H).

Example 34 Potassium Ion Channel Opener Activity Test (FDSS/μCELL Detection)

1. Experimental Method

1.1 Experimental Procedure

Cell preparation: CHO-KCNQ2 cells were cultured in a 175 $cm^2$ culture flask, and when the cell density grew to 60-80%, the culture medium was removed, washed with 7 mL PBS (Phosphate Buffered Saline) once, then 3 mL 0.25% Trypsin was added to digest. After the digestion was completed, 7 mL culture medium (90% DMEM/F12+10% FBS±500 μg/mL G418) was added to neutralize, centrifugated for 3 minutes at 800 rpm. The supernatant was aspirated, then 5 mL culture medium was added to resuspend, and then the cells were counted.

Cell plating: according to the results of cell counting, the density was adjusted to $3\times10^4$ cells/well. After standing at room temperature for 30 minutes, the plate was placed in a 37° C. $CO_2$ incubator and incubated overnight for 16-18 hours. The cell density reached about 80%.

Fluorescent dye incubation: the cell culture medium was discarded, 80 μL/well loading buffer was added, and incubated in the dark at room temperature for 60 minutes. Compound incubation: the loading buffer was discarded, 80 μL/well prepared compound solution was added, and incubated in the dark at room temperature for 20 minutes.

Fluorescence data collection: FDSS/μCELL instrument was used for real-time fluorescence signal recording with excitation wavelength at 480 nm and emission wavelength at 540 nm, recorded 1 time per second, and 20 μL/well stimulation buffer was started to add after recording for 10 seconds for baseline, and then continued to record until the end of 180 seconds.

1.2 Solution Preparation

Loading buffer: 10 mL/plate, the preparation method was as follows:

| Ingredient | Volume |
|---|---|
| PowerLoad ™ concentrate, 100X (ingredient C) | 100 μL |

-continued

| Ingredient | Volume |
|---|---|
| FluxOR ™ reagent, reconstituted in DMSO (step 1.2) | 10 μL |
| Deionized water | 8.8 mL |
| FluxOR ™ test buffer, 10X (ingredient B) | 1 mL |
| Probenecid, reconstituted in deionized water (step 1.1 ) | 100 μL |
| Total volume | 10 mL |

Test buffer sample: 100 mL/plate, the preparation method was as follows:

| Ingredient | Volume |
|---|---|
| Deionized water | 8.9 mL |
| FLuxOR ™ test buffer, 10X (ingredient B) | 1 mL |
| Probenecid, reconstituted in deionized water (step 1.1) | 100 μL |
| Total volume | 10 mL |

Stimulation buffer: 5 mL/plate, the preparation method was as follows:

| | Volume | |
|---|---|---|
| Ingredient | $+K^+$ | $-K^+$ |
| Deionized water | 2.5 mL | 3.5 mL |
| FluxOR ™ Chlorine-free buffer, 5X (ingredient E) | 1 mL | 1 mL |
| $K_2SO_4$ concentrate (125 mM $K_2SO_4$ concentrated solution, ingredient F) | 1 mL | / |
| $Tl_2SO_4$ concentrate (50 mM $Tl_2SO_4$ concentrate, ingredient G) | 0.5 mL | 0.5 mL |
| Total volume | 5 mL | 5 mL |

The above buffer come from a commercially available kit named FluxOR potassium ion channel assay.

1.3 Compound Preparation 20 mM DMSO compound mother liquor was prepared, 10 μL of 20 mM compound mother liquor was took into 20 μL DMSO solution, serially diluted 3 times to 8 intermediate concentrations; then the intermediate concentrations of the compound was took out and added to the test buffer, diluted for 200 times to get the final concentration to be tested, 80 μL was took out and added to the test plate.

The highest test concentration was 100 μM, followed by 100, 33.33, 11.11, 3.70, 1.23, 0.41, 0.137, 0.045 μM, total 8 concentrations. Each concentration set 3 duplicate wells.

The content of DMSO in the final test concentration did not exceed 0.5%. This concentration of DMSO has no effect on the KCNQ2 potassium channel.

1.4 Data Analysis

Experimental data was analyzed by Excel 2007 and GraphPad Prism 5.0 software, and the ratio of 180 seconds was calculated to calculate the agonism effect. The agonism effect of the compound was calculated by the following formula:

$$\text{Percentage of agonism} = \frac{\text{Fluorescence signal ratio with compound} - \text{Fluorescence signal ratio without compound}}{\text{Fluorescence signal ratio without compound}} \times 100\%$$

1.5 Quality Control

Environment: temperature ~25° C.

Reagent: FluxOR™ Detection Kit (Invitrogen, Cat #F0017)

The experimental data in the report must meet the following criteria: Z' Factor>0.5

2. Results: See Table 1, wherein the smaller the $EC_{50}$ is, the higher the activity of the corresponding compound is.

TABLE 1

Test results of some compounds of the present invention

| Compound | Maximum agonist rate (%) | $EC_{50}$ (uM) |
|---|---|---|
| A | 37.97 | 0.44 |
| B | 37.5 | 0.16 |
| D | 29.51 | 0.45 |
| I | 38.3 | 0.44 |
| U | 52.3 | 0.33 |
| O | 29.43 | 0.78 |
| P | 38.22 | 0.034 |
| V | 45.76 | 0.34 |
| W | 33.2 | 0.18 |
| X | 28.94 | 0.072 |
| Y | 37.96 | 0.20 |
| Z | 48.65 | 0.094 |
| A1 | 35.84 | 0.73 |
| A2 | 44.53 | 0.13 |
| A3 | 36.16 | 0.21 |
| A4 | 48.11 | 0.27 |
| A5 | 34.41 | 0.049 |
| A6 | 17.08 | 0.29 |
| A7 | 35.92 | 0.40 |

References for the above test methods:

Zhaobing Gao et al. Journal of Biological Chemistry. 2010, 285(36): 28322-28332.

Example 35 Study on Pharmacokinetics of Mice

1) Research purposes: In order to obtain the pharmacokinetic characteristics and blood-brain barrier of the tested compound in male ICR mice 2) Experimental content Six healthy male ICR mice (body weight range 18-22 g) were taken and divided into 2 groups and 3 mice/group. After fasting overnight (only oral administration group), the compound to be tested was administrated 0.5 mg/kg intravenously and 10 mg/kg orally, blood was collected by jugular vein puncture at time points 0.083 (IV only), 0.25, 0.5, 1, 2, 4, 6 (PO only), 8 and 24 hours, and at least 0.3 mL of whole blood was collected to EDTA-$K_2$ anticoagulant tube. Plasma was centrifuged (6000 rpm, 8 minutes, 4° C.) within half an hour and frozen at −20° C. for later use.

Brain-blood ratio study: 6 healthy male ICR mice (body weight range 18-22 g) were taken and divided into 2 groups and 3 mice/group. After fasting overnight, the compound to be tested (10 mg/kg) was administrated orally respectively. Blood was taken through cardiac puncture at time points 2 and 4 hours, at least 0.5 mL of whole blood was collected to EDTA-$K_2$ anticoagulant tube. Plasma was centrifuged (6000 rpm, 8 minutes, 4° C.) within half an hour and frozen at −20° C. for later use. At the same time, the brain tissue was collected, rinsed with normal saline, then sucked to dryness with absorbent paper, weighed, and frozen at −20° C. for later use.

Experimental results: According to the blood drug concentration data obtained, the non-compartmental model of WinNonlin® 7.0 software (Pharsight, USA) was used to calculate the pharmacokinetic parameters after administration.

TABLE 2

PK Parameters of Single Administration of Male ICR Mice

| Compound | Parameter | Unit | Intravenous 0.5 mg/kg plasma | Gavage 10 mg/kg plasma |
|---|---|---|---|---|
| A | $T_{1/2}$ | (h) | 0.99 | 2.61 |
| | $T_{max}$ | (h) | 0.08 | 0.67 |
| | $C_{max}$ | ng/mL | 269.87 | 141.71 |
| | $AUC_{last}$ | hr*ng/mL | 117.19 | 792.00 |
| | $AUC_{Inf}$ | hr*ng/mL | 118.46 | 793.07 |
| | F | % | / | 33.79 |
| B* | $T_{1/2}$ | (h) | 0.94 | 2.64 |
| | $T_{max}$ | (h) | 0.08 | 0.25 |
| | $C_{max}$ | ng/mL | 404.71 | 776.04 |
| | $AUC_{last}$ | hr*ng/mL | 157.89 | 1398.20 |
| | $AUC_{Inf}$ | hr*ng/mL | 160.65 | 1430.71 |
| | F | % | / | 88.56 |
| I | $T_{1/2}$ | (h) | 0.86 | 3.86 |
| | $T_{max}$ | (h) | 0.08 | 0.33 |
| | $C_{max}$ | ng/mL | 299.07 | 192.09 |
| | $AUC_{last}$ | hr*ng/mL | 107.32 | 528.01 |
| | $AUC_{Inf}$ | hr*ng/mL | 108.23 | 539.24 |
| | F | % | / | 24.6 |
| J* | $T_{1/2}$ | (h) | 0.88 | 1.81 |
| | $T_{max}$ | (h) | 0.08 | 0.25 |
| | $C_{max}$ | ng/mL | 941.95 | 373.91 |
| | $AUC_{last}$ | hr*ng/mL | 361.45 | 693.07 |
| | $AUC_{Inf}$ | hr*ng/mL | 366.13 | 702.68 |
| | F | % | / | 19.18 |
| P | $T_{1/2}$ | (h) | 2.67 | 84.34 |
| | $T_{max}$ | (h) | 0.08 | 8.67 |
| | $C_{max}$ | ng/mL | 382.4 | 315.04 |
| | $AUC_{last}$ | hr*ng/mL | 357.47 | 5989.31 |
| | $AUC_{Inf}$ | hr*ng/mL | 382.98 | 30939.26 |
| | F | % | / | 83.77 |

*Intravenous (IV) dose was 1 mg/kg

TABLE 3

Cerebral blood ratio at each time point after a single oral administration in male ICR mice

| Compound | Time point | Cerebral blood ratio |
|---|---|---|
| A | 2 h | 2.3 |
| | 4 h | 2.8 |
| B | 2 h | 0.99 |
| | 4 h | 0.72 |
| I | 2 h | 6.0 |
| | 4 h | 5.8 |
| J | 2 h | 4.1 |
| | 4 h | 3.2 |
| P | 2 h | 6.4 |
| | 4 h | 5.96 |

The cerebral blood ratio is very important to nerve drugs, and it can be seen from Table 3 that the compounds of the present invention have excellent cerebral blood ratio, which will bring better drug efficacy and excellent safety. By comparing the cerebral blood ratios of compound A, compound 1, compound B and compound J, it can be seen that after the tert-butyl of compound A or compound B has been changed into

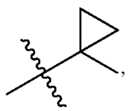 [SMILES: *C1(C)CC1]

the cerebral blood ratio of mice is greatly increased (more than 2 times).

Example 36 Study on Pharmacokinetics of Rats

1) Research purpose: To obtain the pharmacokinetic characteristics of the compounds to be tested in male SD rats.

2) Experimental content

Pharmacokinetic study: 6 healthy male SD rats (SPF grade) were divided into 2 groups and 3 rats/group. After fasting overnight (only oral administration group), compound A was administrated 0.3 mg/kg intravenously and 5 mg/kg orally, blood was collected by jugular vein puncture at time points 0.083 (IV only), 0.25, 0.5, 1, 2, 4, 6 (PO only), 8 and 24 hours, and at least 0.3 mL of whole blood was collected to EDTA-$K_2$ anticoagulant tube. Plasma was centrifuged (6000 rmp, 8 minutes, 4° C.) within half an hour and frozen at −20° C. for later use.

Experimental results: According to the blood drug concentration data obtained, the non-compartmental model of WinNonlin® 7.0 software (Pharsight, USA) was used to calculate the pharmacokinetic parameters after administration.

TABLE 4

PK Parameters of Single Administration in Male SD Rats

| Compound | Parameter | Unit | Intravenous 0.3 mg/kg plasma | Gavage 5 mg/kg plasma |
|---|---|---|---|---|
| A | $T_{1/2}$ | (h) | 0.99 | 3.07 |
| | $T_{max}$ | (h) | 0.08 | 1.50 |
| | $C_{max}$ | ng/mL | 332.50 | 153.65 |
| | $AUC_{last}$ | hr*ng/mL | 140.04 | 908.56 |
| | $AUC_{Inf}$ | hr*ng/mL | 143.95 | 1275.85 |
| | F | % | / | 38.93 |
| B | $T_{1/2}$ | (h) | 2.00 | 3.47 |
| | $T_{max}$ | (h) | 0.08 | 4.00 |
| | $C_{max}$ | ng/mL | 352.07 | 128.07 |
| | $AUC_{last}$ | hr*ng/mL | 146.52 | 1065.52 |
| | $AUC_{Inf}$ | hr*ng/mL | 149.20 | 1075.06 |
| | F | % | / | 43.63 |
| I | $T_{1/2}$ | (h) | 1.74 | 6.25 |
| | $T_{max}$ | (h) | 0.08 | 0.50 |
| | $C_{max}$ | ng/mL | 344.52 | 220.63 |
| | $AUC_{last}$ | hr*ng/mL | 163.75 | 821.65 |
| | $AUC_{Inf}$ | hr*ng/mL | 165.96 | 854.61 |
| | F | % | / | 30.11 |

All literatures mentioned in the present invention are incorporated by reference herein, as though individually incorporated by reference. Additionally, it should be understood that after reading the above teaching, many variations and modifications may be made by the skilled in the art, and these equivalents also fall within the scope as defined by the appended claims.

The invention claimed is:

1. A compound having formula A or a pharmaceutically acceptable salt thereof, formula A

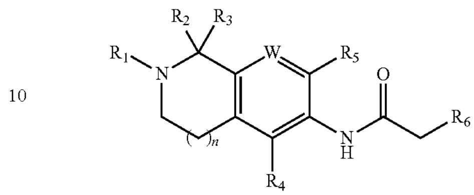

wherein, $R_1$ is a substituted or unsubstituted phenyl group, and the substituted means being substituted by one or more substituents selected from the group consisting of halogen, cyano, $C_{1-6}$ alkyl, $C_{1-6}$ alkoxy, halogenated $C_{1-6}$ alkyl, —$NR_8R_9$, and ethynyl;

$R_2$ and $R_3$ are each independently hydrogen or deuterium;

$R_4$ and $R_5$ are each independently $C_{1-6}$ alkyl;

$R_6$ is selected from the substituted or unsubstituted group consisting of $C_{3-6}$ cycloalkyl and the substituted means being substituted by one or more substituents selected from the group consisting of halogen, $C_{1-6}$ alkyl, $C_{1-6}$ alkoxy, and halogenated $C_{1-6}$ alkyl;

n is 1 or 2;

W is C-$R_7$;

$R_7$ is hydrogen or halogen; and $R_8$ and $R_9$ are each independently $C_{1-6}$ alkyl.

2. The compound of claim 1 or the pharmaceutically acceptable salt thereof, wherein:

$R_4$ and $R_5$ are methyl;

$R_6$ is selected from the substituted or unsubstituted group consisting of $C_{3-6}$ cycloalkyl, and the substituted means being substituted by one or more substituents selected from halogen and $C_{1-6}$ alkyl; and n is 1.

3. The compound of claim 2 or the pharmaceutically acceptable salt thereof, wherein:

$R_6$ is selected from the group consisting of

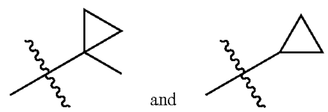

4. The compound of claim 3 or the pharmaceutically acceptable salt thereof, wherein:

$R_6$ is \

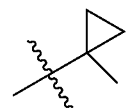

5. A compound having formula A or a pharmaceutically acceptable salt thereof, formula A

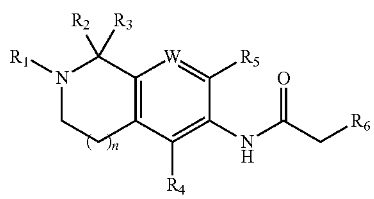

wherein:

$R_1$ is a substituted or unsubstituted phenyl group, and the substituted means being substituted by one or more substituents selected from the group consisting of halogen, cyano, $C_{1-6}$ alkyl, $C_{1-6}$ alkoxy, halogenated $C_{1-6}$ alkyl, —$NR_8R_9$, and ethynyl;

$R_2$ and $R_3$ are each independently hydrogen or deuterium;

$R_4$ and $R_5$ are methyl;

$R_6$ is

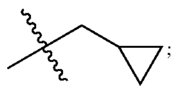 [SMILES: *CC1CC1];

n is 1;

W is C-$R_7$;

$R_7$ is hydrogen or halogen; and $R_8$ and $R_9$ are each independently $C_{1-6}$ alkyl.

6. A compound or the pharmaceutically acceptable salt thereof, wherein the compound is selected from the group consisting of:

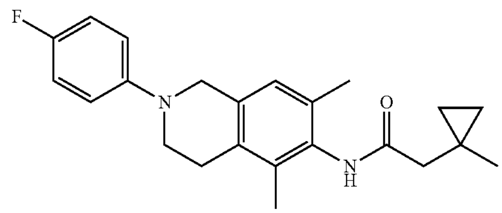

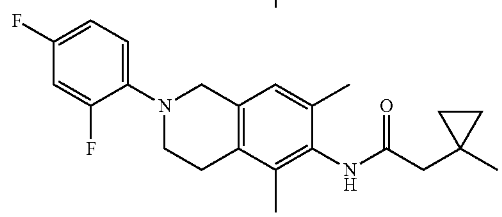

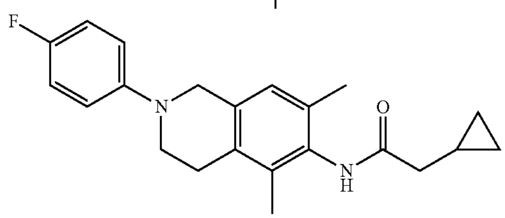

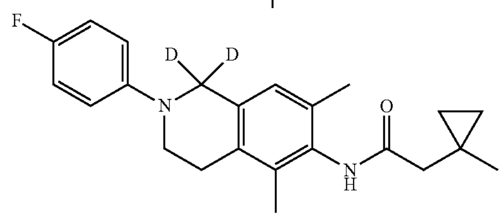

-continued

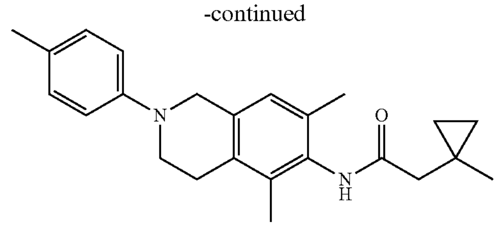

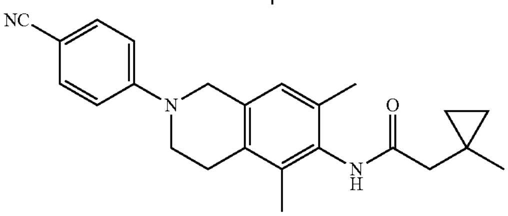

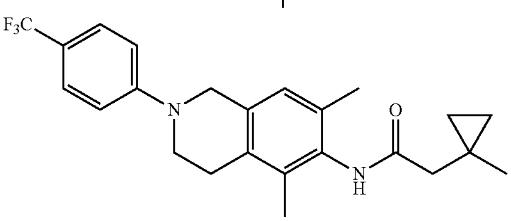

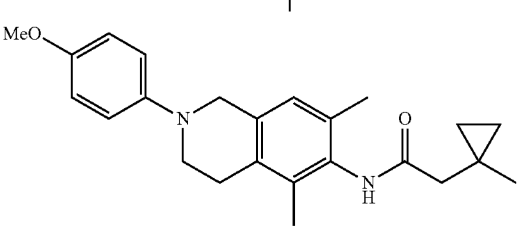

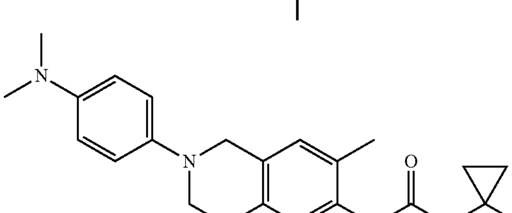

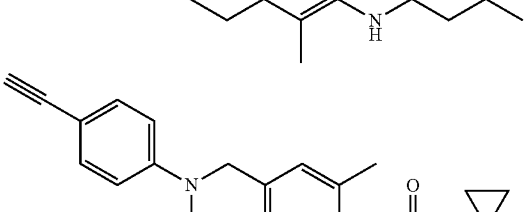

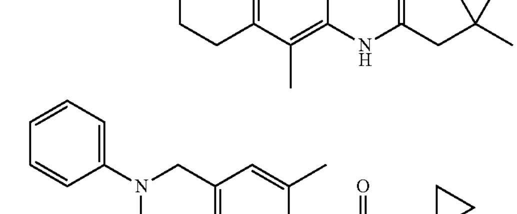

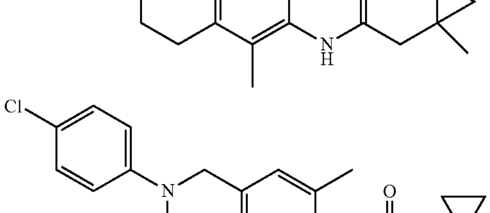

-continued

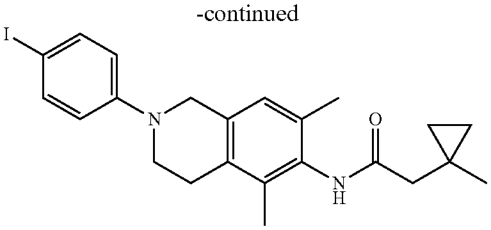

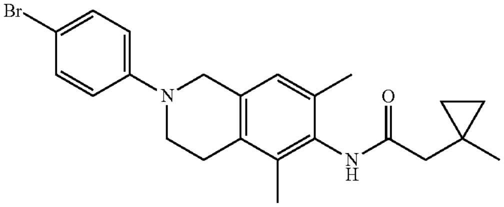

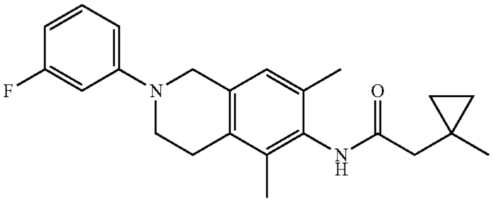

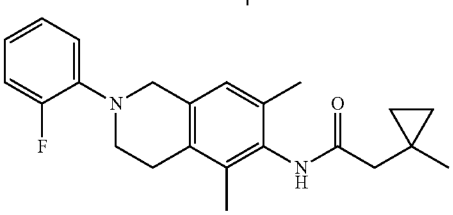

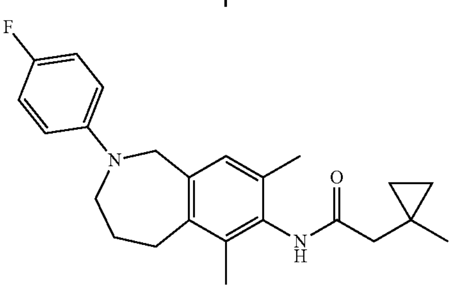

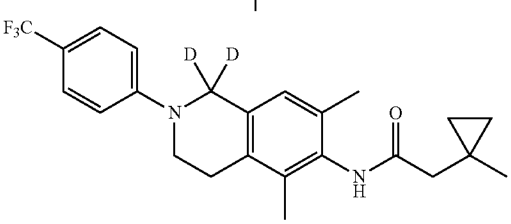

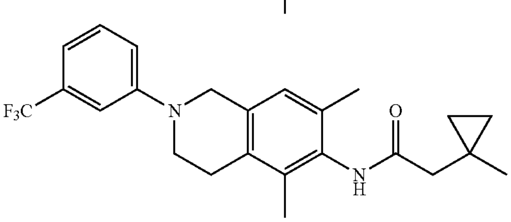

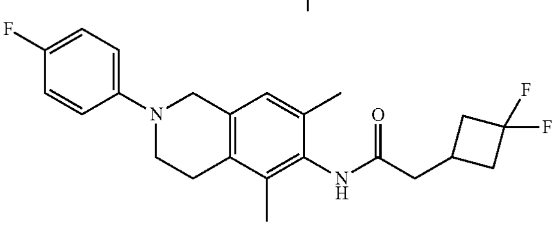

-continued

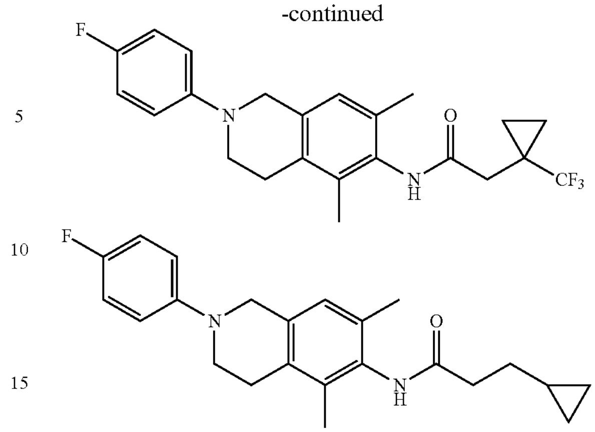

7. A method for preparing the compound of claim 1 or the pharmaceutically acceptable salt thereof comprising the following steps:

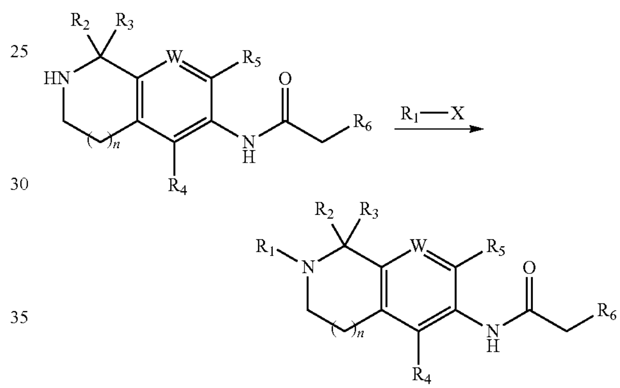

wherein:

X is selected from the group consisting of halogen, —$B(OH)_2$ and —OTf.

8. A pharmaceutical composition comprising one or more pharmaceutically acceptable carriers and a therapeutically effective amount of one or more of the compounds of claim 1 or the pharmaceutically acceptable salts thereof.

9. A medicament for the treatment of a disease sensitive to potassium ion channels, wherein the medicament comprises the compound of claim 1 or the pharmaceutically acceptable salt thereof; wherein the disease sensitive to potassium ion channels is a central nervous system disease, selected from the group consisting of epilepsy, convulsions, inflammatory pain, neuropathic pain, depression, and anxiety disorder.

10. A pharmaceutical composition comprising one or more pharmaceutically acceptable carriers and a therapeutically effective amount of one or more of the compounds of claim 5 or the pharmaceutically acceptable salts thereof.

11. A pharmaceutical composition comprising one or more pharmaceutically acceptable carriers and a therapeutically effective amount of one or more of the compounds of claim 6 or the pharmaceutically acceptable salts thereof.

12. A medicament for the treatment of a disease sensitive to potassium ion channels, wherein the medicament comprises the compound of claim 5 or the pharmaceutically acceptable salt thereof; wherein the disease sensitive to potassium ion channels is a central nervous system disease, selected from the group consisting of epilepsy, convulsions, inflammatory pain, neuropathic pain, depression, and anxiety disorder.

13. A medicament for the treatment of a disease sensitive to potassium ion channels, wherein the medicament comprises the compound of claim 6 or the pharmaceutically acceptable salt thereof; wherein the disease sensitive to potassium ion channels is a central nervous system disease, selected from the group consisting of epilepsy, convulsions, inflammatory pain, neuropathic pain, depression, and anxiety disorder.

* * * * *